(12) United States Patent
Lukhtanov

(10) Patent No.: US 8,163,910 B2
(45) Date of Patent: Apr. 24, 2012

(54) AMIDE-SUBSTITUTED XANTHENE DYES

(75) Inventor: Eugene Lukhtanov, Bothell, WA (US)

(73) Assignee: Elitech Holding B.V., Spankeren (NL)

( * ) Notice: Subject to any disclaimer, the term of this patent is extended or adjusted under 35 U.S.C. 154(b) by 766 days.

(21) Appl. No.: 12/244,712

(22) Filed: Oct. 2, 2008

(65) Prior Publication Data
US 2009/0093612 A1    Apr. 9, 2009

Related U.S. Application Data

(60) Provisional application No. 60/977,316, filed on Oct. 3, 2007.

(51) Int. Cl.
*C07F 9/28* (2006.01)
*C07D 413/10* (2006.01)
*C07K 17/02* (2006.01)

(52) U.S. Cl. .......... 546/23; 544/150; 530/350; 530/300; 549/220

(58) Field of Classification Search .................... 546/23; 544/150; 549/220; 530/300, 350
See application file for complete search history.

(56) References Cited

U.S. PATENT DOCUMENTS 5,681,821 A * 10/1997 Powers et al. ................ 514/20.1

* cited by examiner

*Primary Examiner* — Charanjit Aulakh
(74) *Attorney, Agent, or Firm* — Jackson Walker L.L.P.

(57) ABSTRACT

The present invention provides amide-substituted xanthene fluorescent dyes and reagent for the introduction of phosphonate or sulfo groups into the fluorescent dyes.

33 Claims, 10 Drawing Sheets

Examples of Substituted Xanthenesulfonyl chlorides (Figure 10A)

Mono- and disubstitutedsulfonamidoxanthenes (Figure 10B)

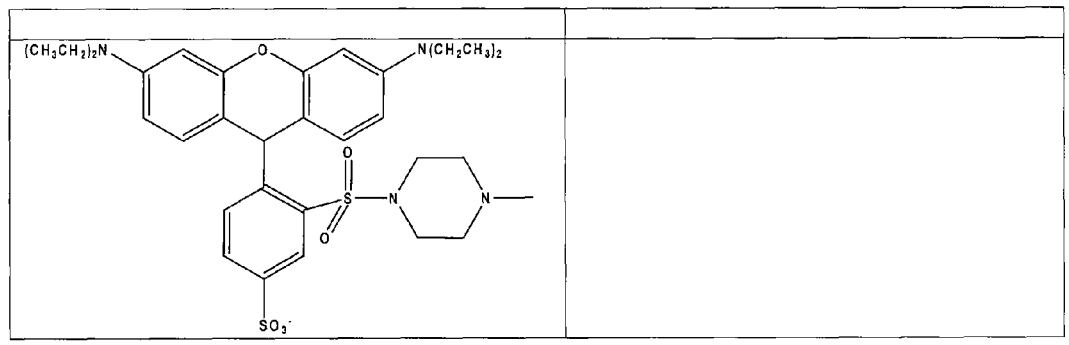
Figure 10 (cont'd)
Structure of Substituted Sulfonylated Xanthene Dyes (Figure 10C)
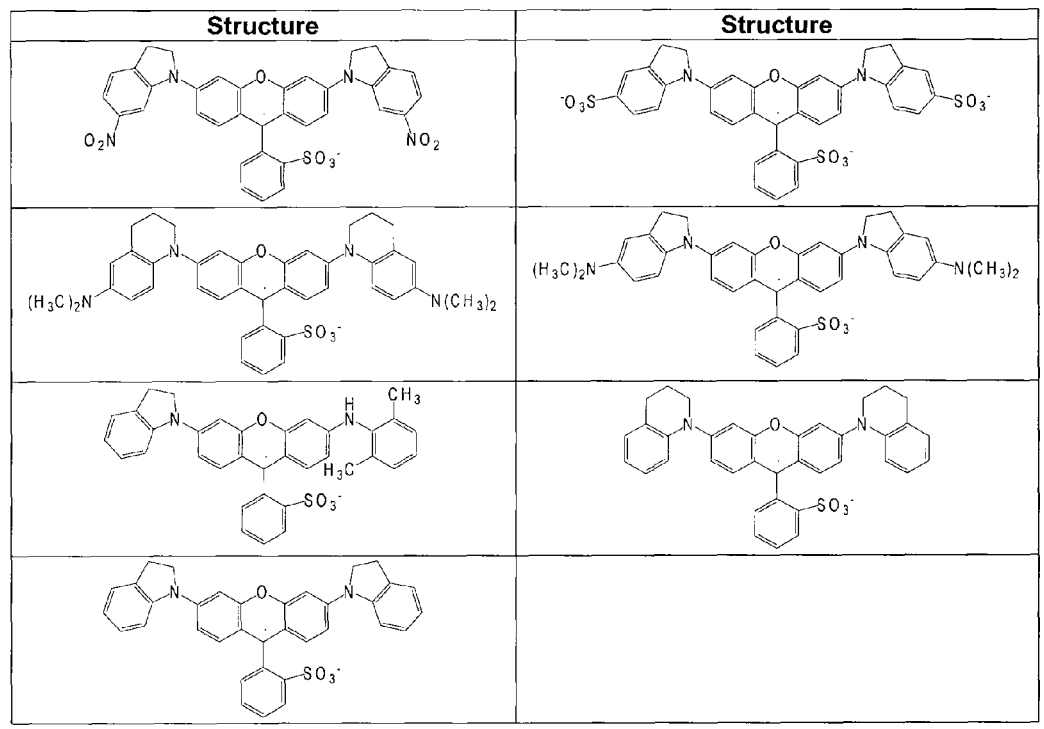

AMIDE-SUBSTITUTED XANTHENE DYES

CROSS-REFERENCES TO RELATED APPLICATIONS

This application claims priority to provisional U.S. Application No. 60/977,316 filed on Oct. 3, 2007, which is incorporated herein by reference for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention provides phosphonate-substituted dyes, including rhodamines, rhodols and fluoresceins that are additionally substituted with 3-amido group. The dyes of the invention, including chemically reactive dyes and dye-conjugates are useful as fluorescent probes, particularly in biological samples.

Xanthenes are among the most commonly used dyes in biological applications where a highly sensitive detection reagent is required. All carboxyphenyl-substituted xanthene dyes belong to three basic structures: fluorescein, rhodamine and rhodol.

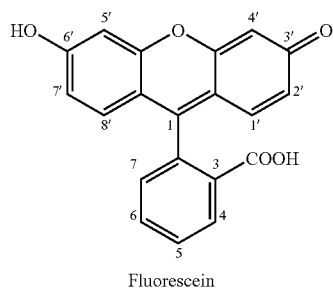

Fluorescein

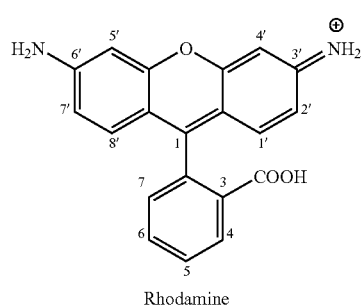

Rhodamine

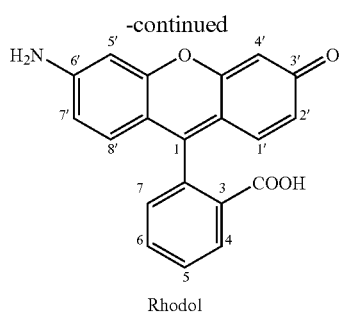

Rhodol

"Fluorescein" dyes include derivatives of 3H-xanthen-6'-ol-3'-one that are typically substituted at the 1-position by an ortho-carboxyphenyl group (hereinafter a 3-carboxyphenyl group, consistent with the numbering above). "Rhodamine" dyes include derivatives of 6'-amino-3H-xanthen-3'-imine that are typically substituted at the 1-position by a 3-carboxyphenyl group. "Rhodol" dyes include derivatives of 6'-amino-3H-xanthen-3'-one that are typically substituted at the 1-position by a 3-carboxyphenyl group. The 3-carboxy group can exist in a free ionized, free protonated or a spiro-lactone form depending on solvent and acidity.

Xanthene dyes have a polycyclic aromatic nature and are generally hydrophobic. Those molecules are also prone to minimize exposure to any hydrophilic environment through interactions with nearby hydrophobic surfaces and residues. These interactions include dye-dye interaction and dye-biomolecule (e.g. proteins, lipids, oligonucleoties) interactions. Hydrophobic interactions can cause substantial quenching effects for fluorescent dyes (see for example Randolph, J. B.; Waggoner, A. S. *Nucleic Acids Res.* 1997, 25(14), 2923-2929 and references cited therein). One method to overcome this problem is to improve the hydrophilic character of the dye by introducing a phosphonate substituent into the dye molecule as disclosed in U.S. application 2006/0199955. Alternatively, sulfonate-substituted dyes can also be utilized as disclosed in U.S. Pat. Nos. 5,268,486 and 6,130,101.

The phosphonate groups disclosed in U.S. application 2006/0199955 have certain advantages over the sulfonate groups. For instance, they do not merely provide the desired negative charge but also introduce functional groups suitable for conjugation with biological agents. However, the activation of the functional groups such as COOH, OH (which requires treatment with acid chlorides), anhydrides, activated esters or various dehydrating agents, is complicated by the concurrent activation of the 3-carboxy group (see U.S. Pat. No. 6,750,357, and U.S. patent application 2006/0154251). The undesired side reaction precludes or significantly reduces the formation of the target mono-activated dyes. Another example of a side reaction involving the 3-carboxy group is described in Lyttle et al. *J. Org. Chem.* 2000; 65(26): 9033-9038. In this example the spiro-lactone form of a rhodamine dye is shown to react with tert-butylamine used for the oligonucleotide deprotection thus generating a 3-carboxamide side product.

It is therefore an object of the present invention to modify phosphonate-substituted xanthene dyes in such a way that the 3-carboxy group may not be capable of undesired side reactions. This object is achieved by substituting the 3-carboxy group with 3-amido group.

The present invention therefore provides phosphonate-substituted dyes, including rhodamines, rhodols and fluoresceins that are additionally substituted with 3-amido group.

The xanthene dyes of the invention possess significant advantages over their carboxy-substituted analogs as well as the non-phosphonylated 3-amidophenyl-xanthenes disclosed in U.S. Pat. Nos. 4,290,955; 4,647,675; 6,399,392; 6,750,357, and U.S. Patent Application No. 2006/0154251, as well as PCT publications WO 2002/055512 and WO 2005/102176. The phosphonate group provides both conjugation capability and additional hydrophilicity to the dye molecules, while the 3-amido substituent blocks undesired side reactions. Overall, the compounds provided herein exhibit increases in aqueous solubility and further exhibit reduced aggregation.

BRIEF SUMMARY OF THE INVENTION

In one aspect, the present invention provides a compound of formula (I):

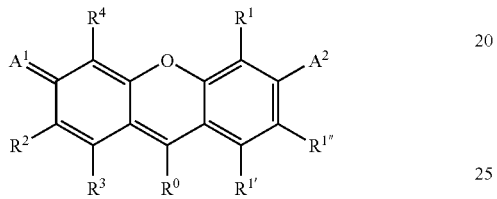

wherein
  $A^1$ is selected from the group consisting of O, N—Z' and $N^+(Z')_2$, wherein at each occurrence Z' is independently hydrogen, $(C_1-C_8)$alkyl, aryl-$(C_1-C_8)$alkyl, aryl or a protecting group; wherein the aliphatic or aryl portions of the Z' group are optionally substituted with halogen, sulfo, phosphono, alkylphosphono, $(C_1-C_4)$alkyl, aryl, $L^f$ or $P^z$; or optionally the Z' group, at each occurrence, independently is combined with $R^2$ or $R^4$ to form a fused 5- to 7-membered ring, and the resultant fused 5- to 7-membered ring is optionally fused to an aryl ring, and is optionally substituted with halogen, $(C_1-C_4)$alkyl, $L^f$ or $P^z$;
  $A^2$ is $OR^w$ or $N(Z'')_2$, wherein each Z" is independently hydrogen, $(C_1-C_8)$alkyl, aryl$(C_1-C_8)$alkyl, aryl or a protecting group; wherein the aliphatic or aryl portions of the Z" group are optionally substituted with halogen, $(C_1-C_4)$alkyl, aryl, $L^f$ or $P^z$; or optionally the Z" group, at each occurrence, independently is combined with $R^1$ or $R^{1'''}$ to form a fused 5- to 7-membered ring wherein the resultant fused 5- to 7-membered ring is optionally fused to an aryl ring, and is optionally substituted with halogen, $C_1-C_4$alkyl, aryl, $L^f$ or $P^z$; and the substituent $R^w$ is selected from H, $(C_1-C_8)$alkyl, aryl, aryl$(C_1-C_4)$alkyl, a protecting group and $L^f$;
  $R^{1'''}, R^{1''}, R^1, R^2, R^3$ and $R^4$ are each independently selected from the group consisting of H, halogen, cyano, $CF_3$, sulfo, $(C_1-C_8)$alkyl, $(C_1-C_8)$alkylthio, $(C_1-C_8)$alkoxy, aryl, heteroaryl, $L^f$ and $P^z$, wherein said aryl or heteroaryl group is optionally substituted with $P^z$; or optionally any two of the $R^{1''}, R^{1'''}, R^2$ and $R^3$ substituents that are attached to adjacent ring atoms are combined to form a five or six membered fused ring that is aromatic, non-aromatic or heteroaromatic, and is optionally substituted with $P^z$; and the alkyl portions of any of $R^{1''}, R^{1'''}$ and $R^1$ through $R^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; the aryl or heteroaryl portions of any of $R^{1''}, R^{1'''}$ and $R^1$ through $R^4$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^z$;
  $R^0$ is selected from the group consisting of subformulae (a), (b), (c) and (d):

(a)
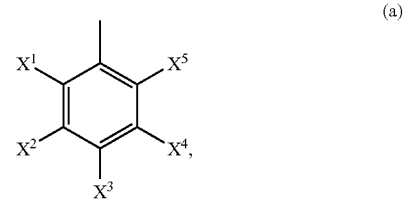

(b)
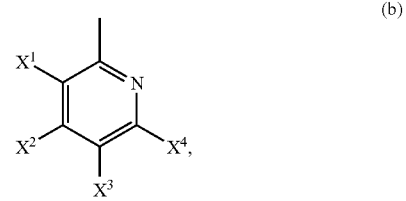

(c)
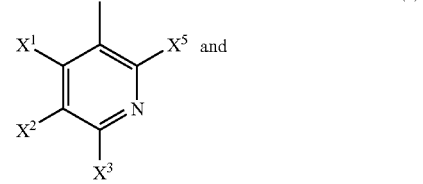

and (d)
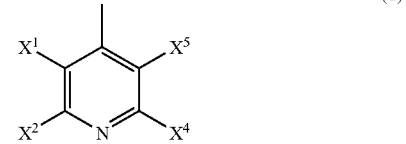

wherein $X^2$, $X^3$ and $X^4$ are each independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, —$SO_3H$, —$PO_3H_2$, —$CO_2H$, $L^f$ and $P^z$;
  $X^1$ and $X^5$ are each independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_2N(R^a)_2$ and $CON(R^a)_2$, and at least one of $X^1$ and $X^5$ is $SO_2N(R^a)_2$ or $CON(R^a)_2$, wherein each $R^a$ is independently selected from H, $(C_1-C_8)$alkyl, hydroxy$(C_1-C_8)$alkyl, protected hydroxy$(C_1-C_8)$alkyl, sulfoalkyl, phosphonoalkyl and alkylphosphonoalkyl, or the two $R^a$ substituents together with the nitrogen atom to which they are attached form a 5- or 6-membered heterocyclic ring having one additional heteroatom selected from O or N; and optionally, any two adjacent substituents of $X^1$ to $X^5$ are combined to form an aromatic or heteroaromatic ring; wherein the aryl or heteroaryl portions of $R^0$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^z$;
  and wherein in formula I, there are from 0 to 1 $L^f$ groups and from 1 to 4 $P^z$ groups, preferably 1 to 2 $P^z$ groups;
  $L^f$ is a linking group having an attached member selected from the group consisting of a protected or unprotected functional group, a reactive group, a polyfunctional linking moiety, a phosphoramidite moiety and a solid support;

P$^z$ is a phosphonate group having a formula selected from (e), (f), (g) and (h):

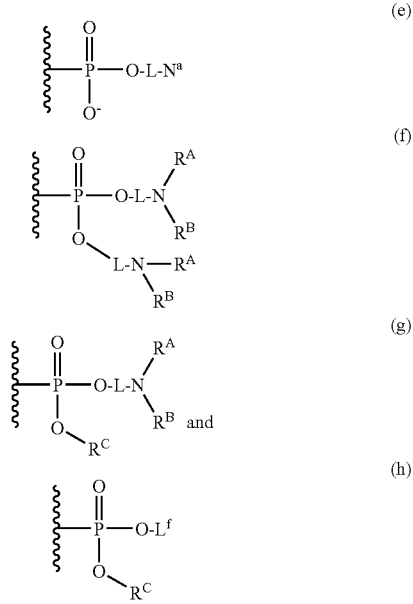

wherein the wavy line indicates the direct attachment to a sp$^2$ carbon of said fluorescent dye; L is a linking group; N$^a$ is an ammonium ion group; each of R$^A$ and R$^B$ is independently selected from the group consisting of H and a labile protecting group; each R$^C$ is selected from the group consisting of H, (C$_1$-C$_8$)alkyl, aryl, aryl(C$_1$-C$_4$)alkyl, a labile protecting group or an alkylene linking group having a distal hydroxy or protected hydroxy group;

and salts thereof.

In another aspect, the present invention provides a phosphonate reagent having the formula:

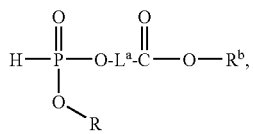

wherein L is a member selected from the group consisting of a (C$_4$-C$_{20}$)alkylene linking group; R$^b$ is selected from the group consisting of t-butyl, tetrahydofuranyl, tetrahydropyranyl, pentafluorophenyl and trialkylsilyl; and R is a labile protecting group selected from t-butyl, —CH$_2$CH$_2$CN, —CH$_2$CH$_2$TMS, —(CH$_2$)$_4$NHC(O)OR$^b$, —(CH$_2$)$_5$NHC(O)OR$^b$ and a phosphate protecting group. Non-limiting exemplary phosphate protecting groups include trihaloalkyl, benzyl, nitrobenzyl, chlorobenzyl, fluorenyl-9-methyl.

In yet another aspect, the present invention provides an oligonucleotide probe. The oligonucleotide probe includes an attached fluorescent reagent of formula (I) and optionally having an attached quencher and a minor groove binding agent. In one embodiment, the attachment of the fluorescent dye reagent to the oligonucleotide is through a functional group present on L$^f$. In another embodiment, the attachment of the fluorescent dye reagent to the oligonucleotide is through a functional group present on P$^z$.

In still another aspect, the present invention provides a biological agent conjugate. The biological agent conjugate includes an attached fluorescent reagent of formula (I) and optionally having an attached quencher and a minor groove binding agent. In one embodiment, the attachment of the fluorescent dye reagent to the biological agent is through a functional group present on L$^f$. In another embodiment, the attachment of the fluorescent dye reagent to the biological agent is through a functional group present on P$^z$.

DETAILED DESCRIPTION OF THE INVENTION

Figure 1:
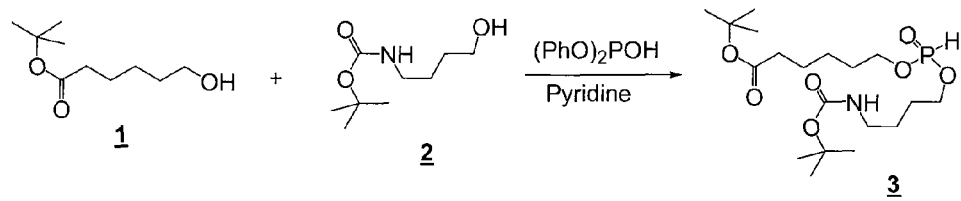
FIG. 1 illustrates the synthesis of an unsymmetric phosphonate reagent tert-butyl 6-{[oxido(3'-{(tert-butoxycarbonyl)-amino}butyl)phosphino]oxy}hexanoate.

Unless otherwise stated, the following terms used in the specification and claims have the meanings given below:

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, (C$_1$-C$_8$)alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, arylalkoxy), when a prefix is not included to indicate the number of main chain carbon atoms in an alkyl portion, the radical or portion thereof will have eight or fewer main chain carbon atoms.

The term "alkylene" means a linear saturated divalent hydrocarbon radical or a branched saturated divalent hydrocarbon radical having the number of carbon atoms indicated in the prefix. For example, (C$_1$-C$_6$)alkylene is meant to include methylene, ethylene, propylene, 2-methylpropylene, pentylene, and the like.

The term "alkenyl" refers to a linear monovalent hydrocarbon radical or a branched monovalent hydrocarbon radical having the number of carbon atoms indicated in the prefix and containing at least one double bond. For example, (C$_2$-C$_6$) alkenyl is meant to include, ethenyl, propenyl, and the like.

The term "alkynyl" refers to a linear monovalent hydrocarbon radical or a branched monovalent hydrocarbon radical containing at least one triple bond and having the number of carbon atoms indicated in the prefix. For example, $(C_2-C_6)$ alkynyl is meant to include ethynyl, propynyl, and the like.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "amido" as used herein, means a monovalent radical represented by formula —NR'(CO)R" or (R'R")$_2$N (CO)—, where R' and R" are each independently H, alkyl, cycloalkyl, heterocycloalkyl, heterocyclic, heteroalkyl, aryl and heteroaryl as defined herein.

The term "aryl" means a monovalent monocyclic, bicyclic or polycyclic aromatic hydrocarbon radical of 5 to 10 ring atoms which is unsubstituted or substituted independently with one to four substituents, preferably one, two, or three substituents selected from alkyl, cycloalkyl, cycloalkyl-alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$—CONR'''R'''' (where n is an integer from 0 to 5, R' and R" are independently hydrogen or alkyl, and R''' and R'''' are, independently of each other, hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one or more heteroatoms or heteroatom functional groups have replaced a ring carbon, while retaining aromatic properties, e.g., pyridyl, quinolinyl, quinazolinyl, thienyl, and the like. For brevity, the term aryl, when used in combination with other radicals (e.g., aryloxy, arylalkyl) is meant to include both aryl groups and heteroaryl groups as described above.

The term "arylalkyl" refers to a radical —R'R" where R' is an alkylene group (having the indicated number of carbon atoms, or if unspecified having six or fewer main chain carbon atoms) and R" is an aryl group or heteroaryl group as defined herein. Examples of arylalkyl groups include benzyl, phenylethyl, 3-(3-chlorophenyl)-2-methylpentyl and the like.

Similarly the term "arylalkenyl" means a radical —R'R" where R' is an alkenylene group and R" is an aryl group or heteroaryl as defined herein, e.g., 3-phenyl-2-propenyl, and the like.

"Arylheteroalkyl" means a radical —R'R" where R' is an heteroalkylene group (having the indicated number of carbon atoms) and R" is an aryl group as defined herein, e.g., 2-hydroxy-2-phenyl-ethyl, 2-hydroxy-1-hydroxymethyl-2-phenyl-ethyl, and the like.

The term "aryloxy", refers to a radical —OR' where R' is an aryl or heteroaryl group, e.g., phenoxy, naphthyloxy and the like.

The prefix "halo" and the term "halogen" when used to describe a substituent, refer to —F, —Cl, —Br and —I.

The term "heteroalkyl" refers to an alkyl radical as defined herein with one, two or three substituents independently selected from cyano, —OR', —NR"R''', and —S(O)$_n$R'''' (where n is an integer from 0 to 2), with the understanding that the point of attachment of the heteroalkyl radical is through a carbon atom of the heteroalkyl radical. R' is hydrogen, alkyl, aryl, arylalkyl, alkoxycarbonyl, aryloxycarbonyl, carboxamido, or mono- or di-alkylcarbamoyl. R" is hydrogen, alkyl, aryl or arylalkyl. R''' is hydrogen, alkyl, aryl, arylalkyl, alkoxycarbonyl, aryloxycarbonyl, carboxamido, mono- or di-alkylcarbamoyl or alkylsulfonyl. R'''' is hydrogen (provided that n is 0), alkyl, aryl, arylalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R', R", R''', and R'''' can be further substituted by NH$_2$, fluorine, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —OR', —NR"R''', or —S(O)$_n$R'''' portions.

The term "heterocyclic" refers to a saturated or unsaturated non-aromatic cyclic radical of 3 to 8 ring atoms in which one or two ring atoms are heteroatoms selected from O, NR (where R is independently hydrogen or alkyl) or S(O)$_n$ (where n is an integer from 0 to 2), the remaining ring atoms being C, where one or two C atoms may optionally be replaced by a carbonyl group. The heterocyclic ring may be optionally substituted independently with one, two, or three substituents selected from alkyl, halo, cyano, hydroxy, alkoxy, amino, mono-alkylamino, di-alkylamino, haloalkyl, haloalkoxy, —COR$^x$ (where R$^x$ is hydrogen, alkyl, cycloalkyl, cycloalkyl-alkyl, phenyl or phenylalkyl), —(CR'R")$_n$—COOR$^x$ (n is an integer from 0 to 5, R' and R" are independently hydrogen or alkyl, and R$^x$ is hydrogen, alkyl, cycloalkyl, cycloalkyl-alkyl, phenyl or phenylalkyl), or —(CR'R")$_n$—CONR'''R'''' (where n is an integer from 0 to 5, R' and R" are independently hydrogen or alkyl, and R$^a$ and R$^b$ are, independently of each other, hydrogen, alkyl, phenyl or phenylalkyl). More specifically the term heterocyclic includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3$-$C_{10}$) refers to the total number of carbon atoms in the portion of the heterocyclic group exclusive of the number of heteroatoms.

The terms "heteroalkylene" means a linear saturated divalent hydrocarbon radical of one to six carbons or a branched saturated hydrocarbon radical of three to six carbon atoms with one, two or three substituents independently selected from —OR', —NR"R''', and —S(O)$_n$R'''' (where n is an integer from 0 to 2) where, R', R", R''' and R'''' are as defined herein for a heteroalkyl radical. Examples include, 2-hydroxyethan-1,2-diyl, 2-hydroxypropan-1,3-diyl and the like.

In some embodiments the alkyl and heteroalkyl groups will be substituted. Substituents for the alkyl and heteroalkyl radicals (including those groups often referred to as alkylene, alkenyl, heteroalkylene, heteroalkenyl, alkynyl, heterocycloalkyl, and heterocycloalkenyl) can be a variety of groups selected from: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR"R", —CN and —NO$_2$ in a number ranging from zero to four, preferably, zero, one, two or three substituents. R', R" and R''' each independently refer to hydrogen, unsubstituted $(C_1$-$C_8)$alkyl and heteroalkyl, unsubstituted aryl, aryl substituted with 1-3 halogens, unsubstituted alkyl, alkoxy or thioalkoxy groups, or aryl-($C_1$-$C_4$) alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl.

Substituents for the aryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

The term "sulfo" means a sulfo group, —$SO_3$H, or its salts.

The term "sulfoalkyl" means an alkyl group to which a sulfo group is bonded, wherein the alkyl is bonded to the molecule of interest.

The term "phosphono" means a phosphono group, —$PO_3H_2$ or it salts.

The term "phosphonoalkyl" means an alkyl group to which a phosphono group is bonded, wherein the alkyl is bonded to the molecule of interest. Non-limiting phosphonoalkyl groups include phosphonomethyl, phosphonoethyl, phosphonopropyl, phosphonoisopropyl, phosphonobutyl, phosphonoisobutyl, phosphonopentyl, phosphonoisopentyl, phosphonohexyl, phosphonoisohexyl, phosphonoheptyl, phosphonooctyl, phosphonoisooctyl and isomers thereof.

The term "alkylphosphono" means a radical —P(O)(OR')(OR"), where R' and R" are alkyl or —H with the proviso that R' and R" are not both —H. Non-limiting alkylphosphono groups include methylphosphono, ethylphosphono, propylphosphono, isopropylphosphono, butylphosphono, isobutylphosphono, pentylphosphono, isopentylphosphono, hexylphosphono, isohexylphosphon, heptylphosphono, octylphosphono and isooctylphosphono and isomers thereof.

Certain compounds or oligonucleotides of the present invention may exist in a salt form. Such salts include base addition salts such as sodium, potassium, calcium, ammonium, organic amino, or magnesium salt, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of ADVANCED ORGANIC CHEMISTRY, 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not (e.g, $^2$H), are intended to be encompassed within the scope of the present invention.

"Protecting group" or "protected form thereof" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like (see also, Boyle, A. L. (Editor), CURRENT PROTOCOLS IN NUCLEIC ACID CHEMISTRY, John Wiley and Sons, New York, Volume 1, 2000). Representative hydroxy protecting groups include those where the hydroxy group is either acylated or alkylated such as benzyl and trityl ethers as well as alkyl ethers, tetrahydrofuranyl ethers, tetrahydropyranyl ethers, trialkylsilyl ethers and allyl ethers. Additionally, hydroxy group can be protected by formation of carbonates, such as alkyl carbonates or aryl carbonates. Exemplary carbonates include alkyl methyl carbonate, alkyl 9-fluorenylmethyl carbonate and alkyl p-nitrophenyl carbonate. Furthermore, hydroxy groups can be protected by photoremovable groups such as α-methyl-6-nitropiperonyloxycarbonyl (McGall, G. H. and Fidanza, J. A., Photolithographic synthesis of high-density oligonucleotide arrays, in DNA ARRAYS METHODS AND PROTOCOLS, Edited by Rampal J. B., METHODS IN MOLECULAR BIOLOGY, 170:71-101 (2001), Humana Press, Inc., NY; Boyle, Ann L. (Editor), Current Protocols in Nucleic Acid Chemistry, John Wiley and Sons, New York, Volume 1, 2000). Representative phosphate protecting groups include alkyl, such as methyl, ethyl, isopropyl, t-butyl, cyclohexyl and 1-adamantyl; 2-substituted ethyl, such as 2-cyanoethyl, 2-(trimethylsilyl)ethyl, 2-(4-nitrophenyl)ethyl, 2-(triphenylsilyl)ethyl, 2-(2'-pyridyl)ethyl, 2(4'-pyridylethyl) and the like; trihaloethyl, such as trichloroethyl, tribromoethyl, trifluoroethyl and the like; benzyl, substituted benzyl, such as chlorobenzyl and nitrobenzyl; fluoroenyl-9-methyl; phenyl, substituted phenyl, such as chlorophenyl, nitrophenyl and the like.

The term "labile protecting group" refers to those protecting groups that are removeable under mild conditions that do not significantly impact the remainder of the molecule.

As used herein, the term "reactive group" refers to an electrophilic group or a nucleophilic group that can be used to form a covalent linkage with another component. Examples of nucleophilic groups include $-NH_2$, $-NHNH_2$, $-ONH_2$, $-NHC=(O)NHNH_2$, $-OH$, $-COOH$, or $-SH$. The electrophilic groups can be activated esters, acrylamides, acyl azides, acyl halides, aldehyde or ketones, alkyl halides, alkyl sulfonates, anhydrides, aryl halides, aziridines, boranates, carboxylic acids, carbodiimides, diazoalkanes, epoxides, haloacetamides, halotriazines, imidoesters, isocyanates, isothiocyanates, maleimides, phophoramidites, silyl halides, sulfonate ester and sulfonyl halides. Additionally, a spacer can include hetero atoms in linear or acyclic portions, cyclic portions, aromatic rings or combinations thereof. Within the above, an "activated ester group" refers to a carboxylic acid ester which is more reactive than an alkyl ester (e.g., methyl ester) in reactions in which the carbonyl moiety is an electrophilic center toward, for example, amide formation. Examples of activated esters include pentafluorophenyl (PFP) esters, N-hydroxysuccinimide esters, and the like.

A "polyfunctional linking moiety" is a linking group having two or more functional groups that can be used to attach or conjugate two or more components that can be the same or different. Polyfunctional linking moieties include, for example, trivalent linking groups and tetravalenet linking groups (see, for example, U.S. Pat. Nos. 5,512,677; 5,419,966; 5,585,481; 5,942,610 and 5,736,626).

A "phosphoramidite" is a term of art used to refer to a trivalent phosphorus group typically used in oligonucleotide synthesis. Detailed descriptions of the chemistry used to form oligonucleotides by the phosphoramidite method are provided in Caruthers et al., U.S. Pat. Nos. 4,458,066 and 4,415,732; Caruthers et al., *Genetic Engineering*, 4:1-17 (1982); Users Manual Model 392 and 394 Polynucleotide Synthesizers, pages 6-1 through 6-22, Applied Biosystems, Part No. 901237 (1991), each of which are incorporated by reference in their entirety. Labeled oligonucleotides can be synthesized enzymatically, e.g., using a DNA polymerase or ligase, e.g., Stryer, Biochemistry, W. H. Freeman and Company, 6th Ed. (2006), or by chemical synthesis, e.g., by a phosphoramidite method, a phosphite-triester method, and the like, e.g., Gait, OLIGONUCLEOTIDE SYNTHESIS, IRL Press (1990). Labels can be introduced during enzymatic synthesis utilizing labeled nucleoside triphosphate monomers, or introduced during chemical synthesis using labeled non-nucleotide or nucleotide phosphoramidites, or may be introduced subsequent to synthesis. A typical phosphoramidite reagent used in oligonucleotide synthesis is represented by the structure below:

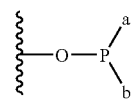

wherein the wavy line indicates the attachment to the remainder of the reagent and the substituents "a" and "b" are each independently isopropyl amino, diisopropylamino, 2-cyanoethyloxy, methoxy or morpholino; and "a" and "b" are not the same.

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

The term "biological agent" refers to essentially any nucleoside, oligonucleotide, peptide, protein, aminocarbohydrate or ligand, as well as analogs thereof (e.g., oligonucleotides having modified or non-natural bases).

The term "conjugate" refers to a molecule formed by the covalent attachment of two or more components such as oligonucleotides, fluorophores, quenchers, minor groove binders, and the like.

"Oligonucleotide" and "polynucleotide" are used interchangeably and refer to a polymer of nucleotides, either natural or synthetic including, but not limited to those nucleotides having modified bases, sugar analogs, and the like. As noted above, an oligonucleotide conjugate will refer to an oligonucleotide as defined, having at least one covalently attached fluorophore, quencher, minor groove binder (MGB or MB) or other useful fragments, as well as combinations of the recited components.

The term "solid support" refers to essentially any solid or semisolid matrix that is useful for, and compatible with, automated oligonucleotide techniques and includes, glass, polystyrene, nylon, plastic, combinations and the like. Examples of useful solid supports have been described in, for example, U.S. Pat. Nos. 5,262,530, 5,419,966, 5,512,667 and 5,589, 586.

As used herein, the term "3-substituted phosphonylated dye" and "3-substituted carboxyamide phosphonate dye" both refer to a dye having attached thereto at least one or more phosphonate or functionalized phosphonate groups in addition to a carboxyamide or sulfonamide substitutent in the 3-position of the xanthene dye.

The term "solid substrate" refers to any material that is treated or mixed with an amide dye to produce a desired colored dye-substrate, these include glass, plastic, food, textile, pharmaceutical, cosmetic, printing and biological materials. For example erythrosine, a xanthene dye is used in food, drugs, cosmetics, as a biological stain and color additive (M. O'Neil editor, THE MERCK INDEX, Merck & Co, 14th Edition, Whitehouse Station, N.J. (entry 3693, page 632 (2006)). Processes for dyeing textile materials with xanthene dyes has been described (see U.S. Pat. No. 4,371,371). Additionally, U.S. Pat. No. 4,139,342 discloses dye-impregnated plastics for laser applications, while U.S. Pat. No. 7,192,476 discloses fluorescent xanthene/water based inks for ink-jet recording.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

General

The present invention resides in the discovery that a wide variety of fluorescent dyes (or fluorophores) can be prepared having phosphonate groups and/or zwitterionic phosphonate groups (or a protected form thereof) as well as substituents at the 3-position that lock the dyes in a non-spirolactone form. These reagents are more hydrophilic, can be used in a wide variety of synthetic procedures, are shelf-stable and can be used to label essentially any biological agent (e.g., oligonucleotides, peptides, proteins, probes, and the like). Accordingly, the invention provides new "3-substituted phosphonylated dyes" as well as methods of labeling biological agents using these "3-substituted phosphonylated dyes". The invention further provides reagents such as activated- and phosphoramidite-derivatized dyes that can be prepared from the 3-substituted phosphonate-substituted dyes described herein. Additionally, support-bound dyes, similarly prepared from the phosphonate dyes are also described. Additionally, reactive phosphonylated dyes for labeling biological agents are also disclosed.

The "3-substituted phosphonate or 3'-substituted phosphonylated dyes" (e.g., dyes having a zwitterionic phosphonate group or a protected form thereof), as well as reagents incorporating those dyes (e.g., support-bound dyes, reactive ester groups and phosphoramidites) have been found to be compatible with the xanthene fluorophores that include the fluorescein dyes, rhodol dyes and rhodamine dyes.

Examples of these dye classes can be found in Haugland, et al., HANDBOOK OF FLUORESCENT PROBES AND RESEARCH CHEMICALS, SIXTH ED., Molecular Probes, Eugene, Oreg. 1996; Krasoviskii and Bolotin, ORGANIC LUMINESCENT MATERIALS, VCH Publishers, N.Y., 1988; Zolliger, COLOR CHEMISTRY, 2nd Edition, VCH Publishers, N.Y., 1991. Still other dyes are provided via online sites such as http://www.zeiss.com.

Embodiments of the Invention

In one aspect, the present invention provides a fluorescent dye reagent having formula (I):

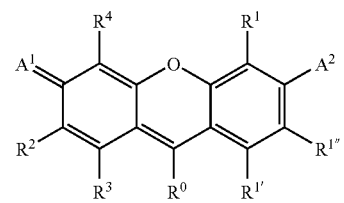

$A^1$ is selected from the group consisting of O, N—Z', or $N^+(Z')_2$, wherein at each occurrence Z' is independently hydrogen, $(C_1-C_8)$alkyl, aryl-$(C_1-C_8)$alkyl, aryl or a protecting group; wherein the aliphatic or aryl portions of the Z' group are optionally substituted with halogen, sulfo, phosphono, alkylphosphono, $(C_1-C_4)$alkyl, aryl, $L^f$ or $P^z$; or optionally the Z' group, at each occurrence, independently is combined with R2 or $R^4$ to form a fused 5- to 7-membered saturated or non-saturated ring, and the resultant fused 5- to 7-membered ring is optionally fused to an aryl ring, and is optionally substituted with halogen, $(C_1-C_4)$alkyl, $L^f$ or $P^z$.

$A^2$ is $OR^w$ or $N(Z'')_2$, wherein each Z'' is independently hydrogen, $(C_1-C_8)$alkyl, aryl$(C_1-C_8)$alkyl, aryl or a protecting group; wherein the aliphatic or aryl portions of the Z'' group are optionally substituted with halogen, $(C_1-C_4)$alkyl, aryl, $L^f$ or $P^z$; or optionally the Z'' group, at each occurrence, independently is combined with $R^1$ or $R^{1'''}$ to form a fused 5- to 7-membered ring wherein the resultant fused 5- to 7-membered saturated or non-saturated ring is optionally fused to an aryl ring, and is optionally substituted with halogen, $C_1-C_4$alkyl, aryl, $L^f$ or $P^z$; and the substituent $R^w$ is selected from H, $(C_1-C_8)$alkyl, aryl, aryl$(C_1-C_4)$alkyl, a protecting group and $L^f$.

$R^{1'}, R^{1'''}, R^1, R^2, R^3$ and $R^4$ are each independently selected from the group consisting of H, halogen, cyano, $CF_3$, sulfo, $(C_1-C_8)$alkyl, $(C_1-C_8)$alkylthio, $(C_1-C_8)$alkoxy, aryl, heteroaryl, $L^f$ and $P^z$, wherein said aryl or heteroaryl group is optionally substituted with $P^z$; or optionally any two of the $R^{1'}, R^{1'''}, R^2$ and $R^3$ substituents that are attached to adjacent ring atoms are combined to form a five or six membered fused ring that is aromatic, non-aromatic or heteroaromatic, and is optionally substituted with $P^z$; and the alkyl portions of any of $R^{1'}, R^{1'''}$ and $R^1$ through $R^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; the aryl or heteroaryl portions of any of $R^{1'}, R^{1'''}$ and $R^1$ through $R^4$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^z$.

$R^O$ is selected from the group consisting of subformulae (a), (b), (c) and (d):

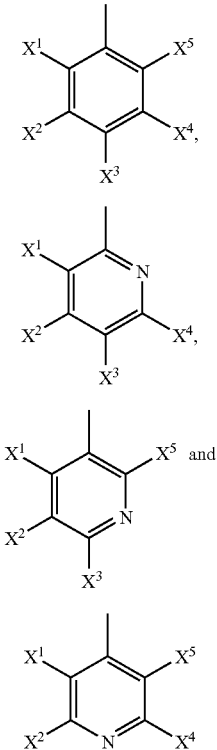

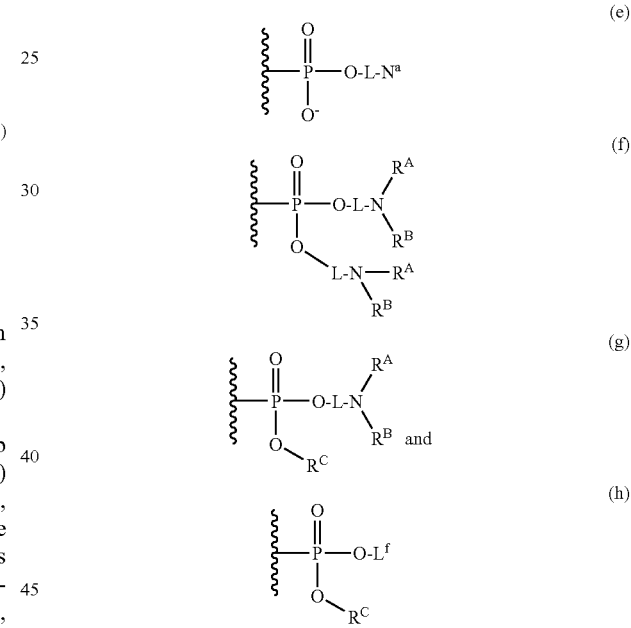

wherein $X^2$, $X^3$ and $X^4$ are each independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$, $PO_3H_2$, $CO_2H$, $L^f$ and $P^z$;

$X^1$ and $X^5$ are each independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_2N(R^a)_2$ and $CON(R^a)_2$, and at least one of $X^1$ and $X^5$ is $SO_2N(R^a)_2$ or $CON(R^a)_2$, wherein each $R^a$ is independently selected from H, $(C_1-C_8)$alkyl, hydroxy$(C_1-C_8)$alkyl, protected hydroxy$(C_1-C_8)$alkyl, sulfoalkyl, phosphonoalkyl and alkylphosphonoalkyl or optionally the two $R^a$ substituents together with the nitrogen atom to which they are attached form a 5- or 6-membered heterocyclic ring having one additional heteroatom selected from O or N; and optionally, any two adjacent substituents of $X^1$ to $X^5$ are combined to form an aromatic or heteroaromatic ring; wherein the aryl or heteroaryl portions of $R^O$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^z$; and wherein in formula I, there are from 0 to 1 $L^f$ groups and from 1 to 4 $P^z$ groups, preferably 1 to 2 $P^z$ groups.

$L^f$ is a linking group having an attached member selected from the group consisting of a protected or unprotected functional group, a reactive group, a polyfunctional linking moiety, a phosphoramidite moiety and a solid support.

$L^f$ can be a variety of linking groups known to those skilled in the art. Many linking groups are available from commercial sources and can be utilized in the reagents above by coupling one end of the linker to the fluorescent dye and the other end of the linker to a protecting group. In one group of embodiments, $L^f$ is a $(C_2-C_{20})$alkylene group, terminating in a functional group such as hydroxy, protected hydroxy, amino, protected amino, carboxy, carboxylate ester, carboxamide, urea, and the like. In other embodiments, $L^f$ is an alkylene group having an attached phosphoramidite moiety, preferably 2-cyanoethyl-N,N-diisopropylphosphoramidite. Similarly, the linking group L can be selected from a variety of linking groups having from 2 to 50 main chain atoms. Examples of linking group include, but are not limited to, alkylene linking groups, heteroalkylene linking groups, polyether linking groups, linking groups containing a combination of acyclic and cyclic groups (e.g., a alkylene group and a heterocyclic group, or a heteroalkylene group and a arylene group), and the like. In some embodiment, the linking group has from 2 to 50 main chain atoms and is a combination of acyclic and cyclic groups.

$P^z$ is a phosphonate group having a formula selected from (e), (f), (g) and (h):

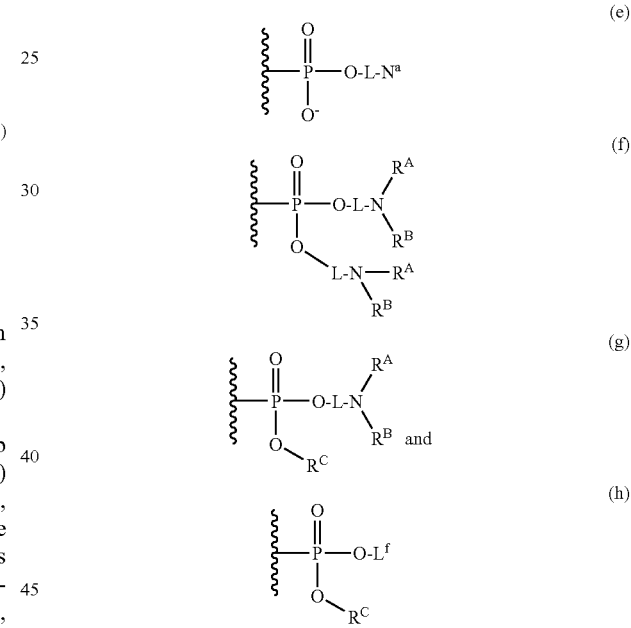

wherein the wavy line indicates the direct attachment to a $sp^2$ carbon of said fluorescent dye; L is a linking group; $N^a$ is an ammonium ion group; each of $R^A$ and $R^B$ is independently selected from the group consisting of H and a labile protecting group; each $R^C$ is selected from the group consisting of H, $(C_1-C_8)$alkyl, aryl, aryl$(C_1-C_4)$alkyl, a labile protecting group or an alkylene linking group having a distal hydroxy or protected hydroxy group; and salts thereof.

In one group of embodiments of compounds having formula I, $A^1$ is selected from the group consisting of =O, $=N^+H(C_1-C_8)$alkyl, $=N^+((C_1-C_8)alkyl)_2$, $=N^+Haryl$, $=N^+((C_1-C_8)alkyl)(aryl)$, $=N^+(aryl)_2$, $=N^+((C_1-C_8)alkyl)(aryl(C_1-C_8)alkyl)$, $=N^+(aryl)(aryl(C_1-C_8)alkyl)$ and $N^+(aryl(C_1-C_8)alkyl)(aryl(C_1-C_8)alkyl)$, optionally substituted with halogen, sulfo, phosphono, alkylphosphono, $(C_1-C_4)$alkyl, aryl, $L^f$ or $P^z$. In certain instances, $A^1$ is =O, $=N^+(Me)_2$, $=N^+(Et)_2$ or $=N^+(CH_3)(CH_2CH_2SO_3^-)$.

In another group of embodiments of compounds having formula (I), symbol:
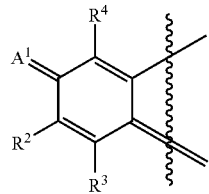
in formula (I) is selected from the group consisting of:
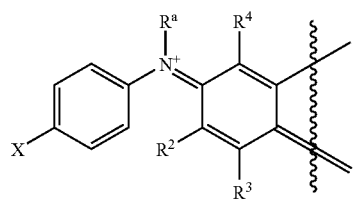
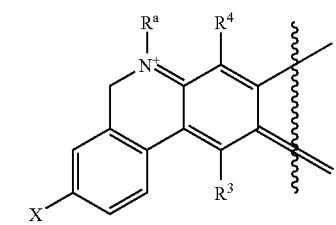
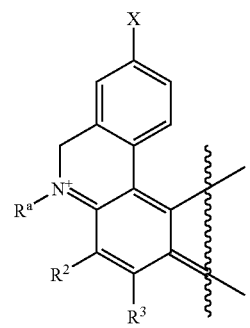
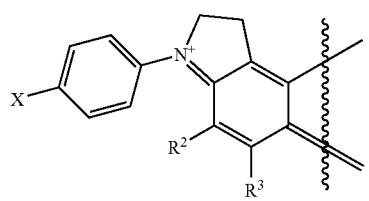
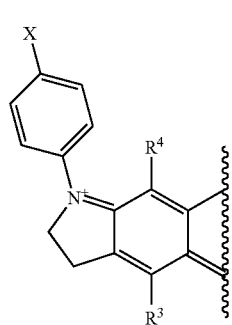 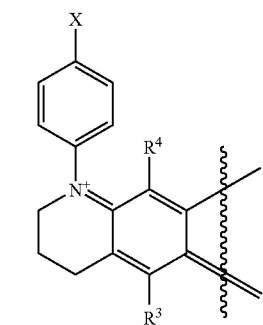
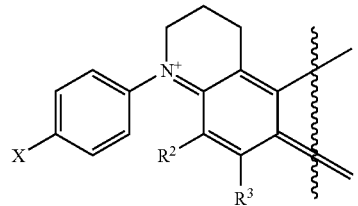
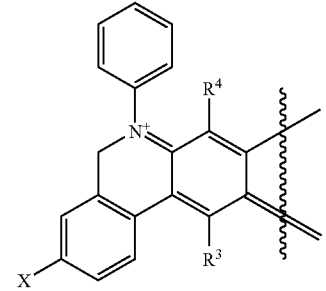
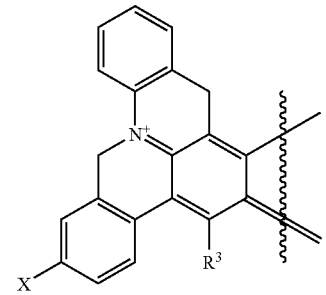
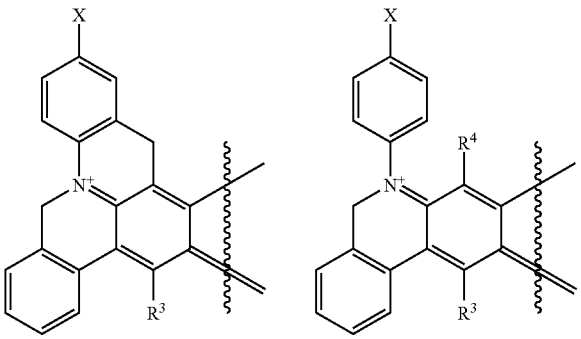
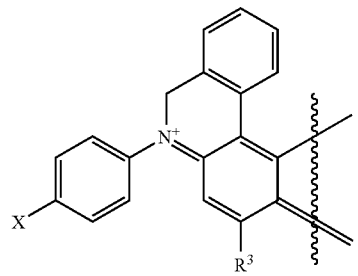
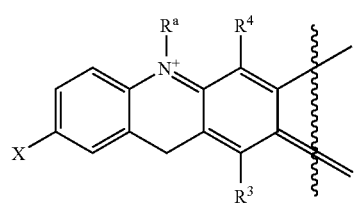

-continued
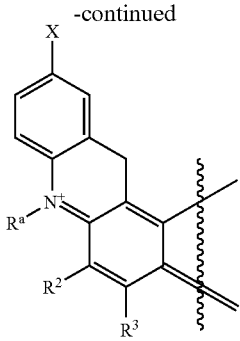
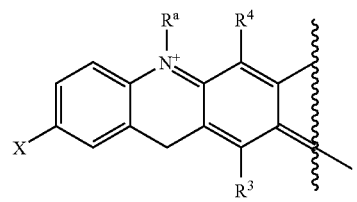
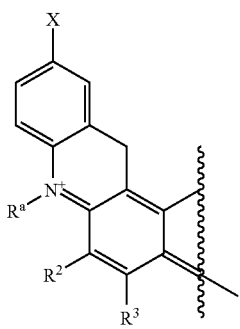
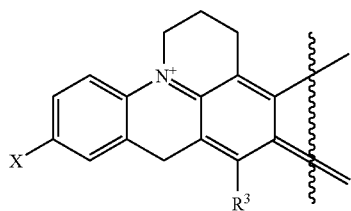
and
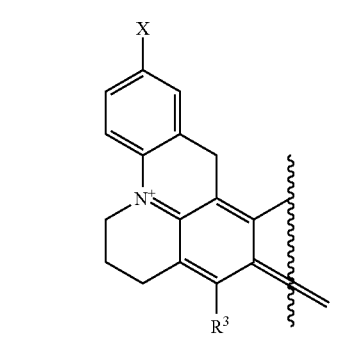
where X is a halogen, and $R^a$, $R^2$, $R^3$ and $R^4$ are as defined above.
In yet another group of embodiments of compounds having formula (I), symbol:
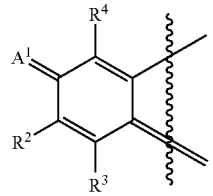
in formula (I) is selected from the group consisting of:
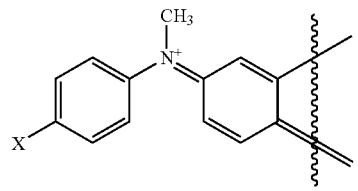
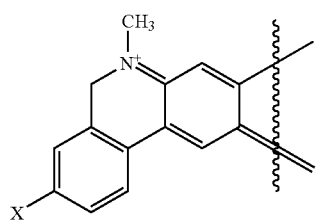
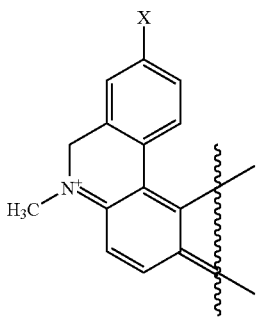
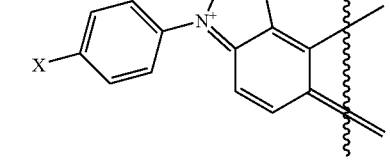
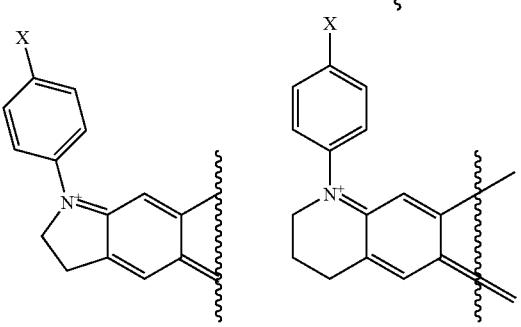

-continued

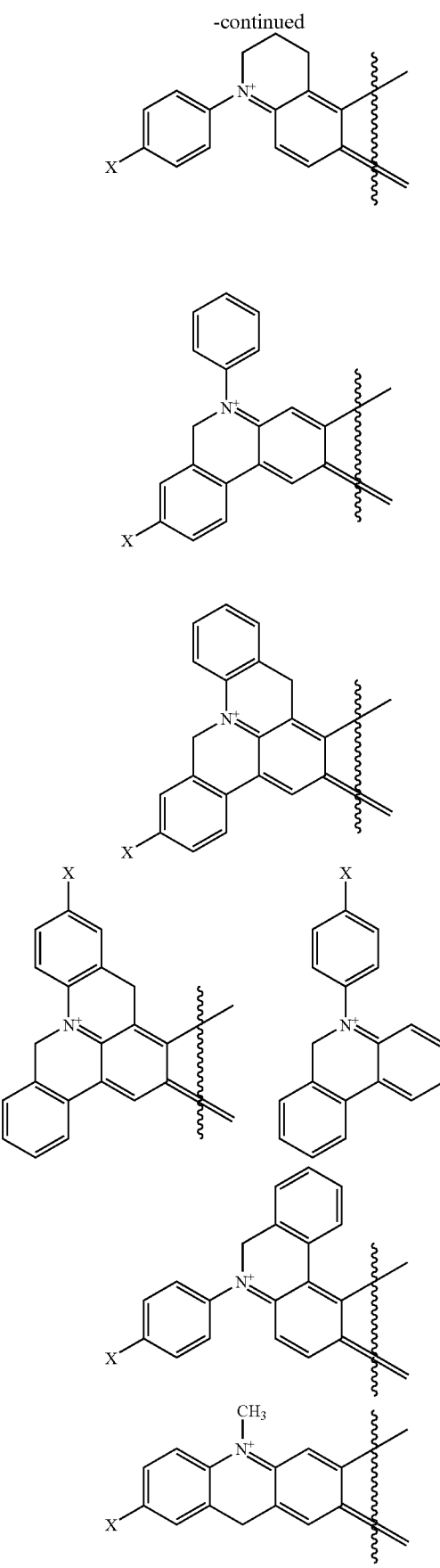
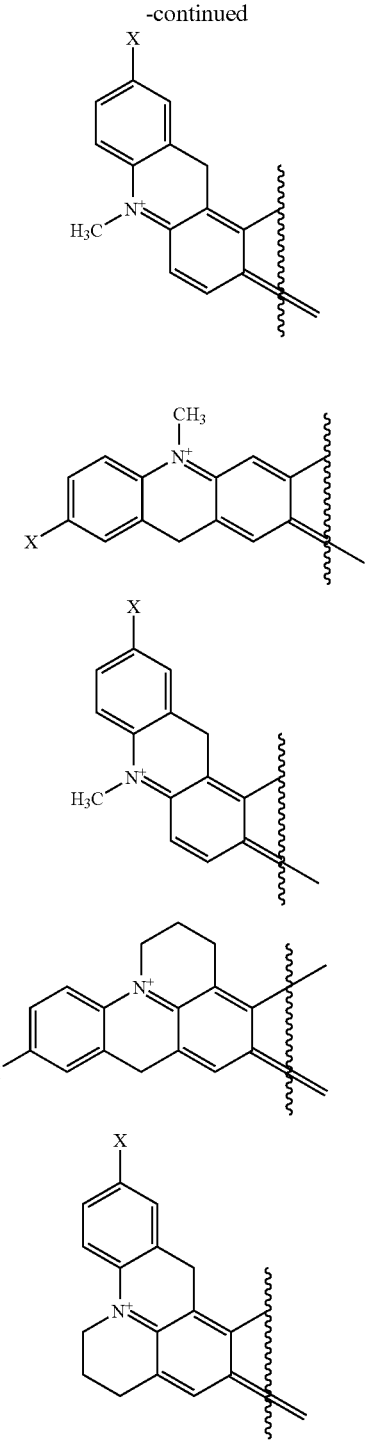

where X is a halogen.

In one group of embodiments of compounds having formula I, $A^2$ is selected from the group consisting of —$OR^a$, —NH($C_1$-$C_8$)alkyl, —N(($C_1$-$C_8$)alkyl)$_2$, —NH-aryl, —N(($C_1$-$C_8$)alkyl)(aryl), —N(aryl)$_2$, —N(($C_1$-$C_8$)alkyl)(aryl($C_1$-$C_8$)alkyl), —N(aryl)(aryl($C_1$-$C_8$)alkyl) and —N(aryl($C_1$-$C_8$)alkyl)(aryl($C_1$-$C_8$)alkyl), optionally substituted with halogen, sulfo, phosphono, alkylphosphono, ($C_1$-$C_4$)alkyl, aryl, $L^f$ or $P^z$. In certain instances, $A^2$ is —OH, —N(Me)$_2$, —N(Et)$_2$ or —N(CH$_3$)(CH$_2$CH$_2$SO$_3^-$).

In another group of embodiments of compounds having formula I, symbol:
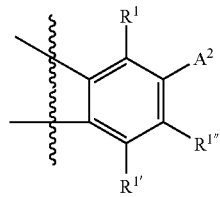
in formula (I) is selected from the group consisting of:
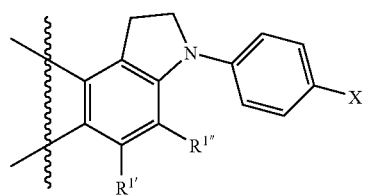
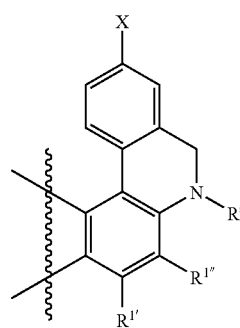
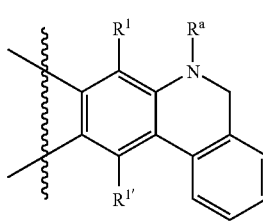
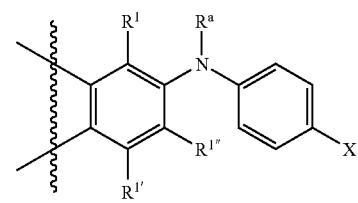
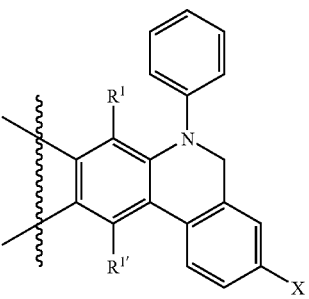
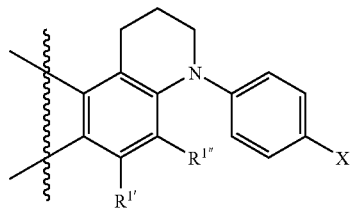
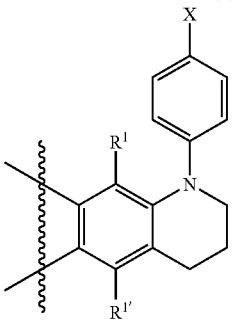
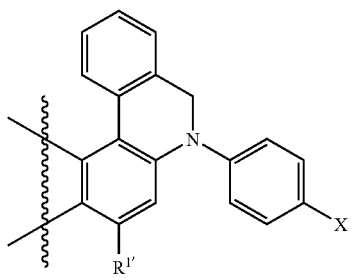
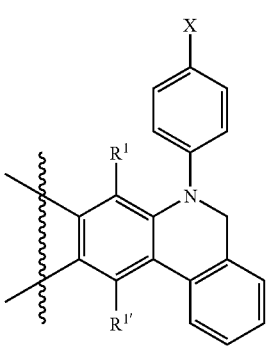
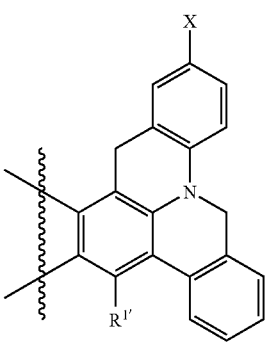
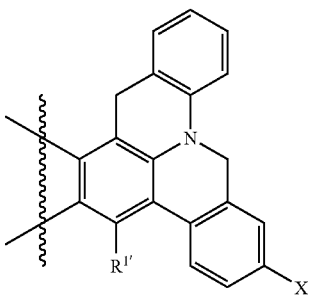
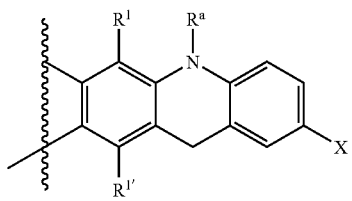

-continued
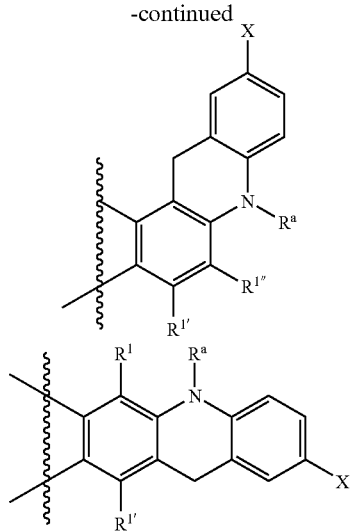
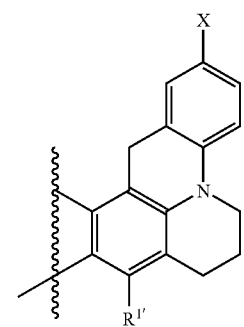
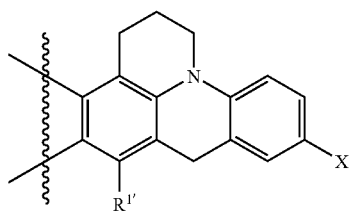
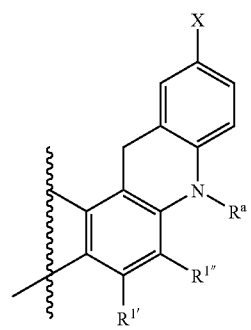
where X is a halogen, and $R^a$, $R^1$, $R^{1'}$, $R^{1''}$ are as defined above.
In yet another group of embodiments of compounds having formula I, symbol:
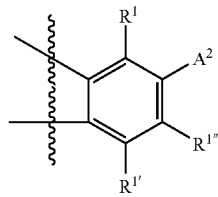
in formula (I) is selected from the group consisting of:
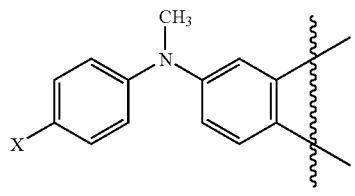
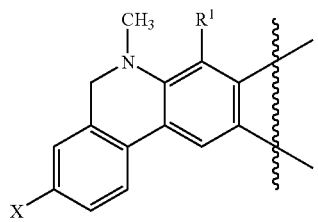
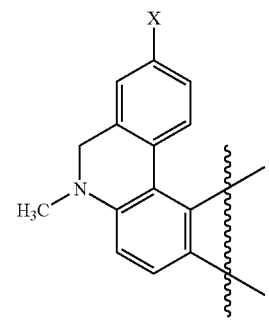
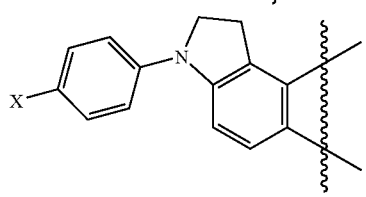
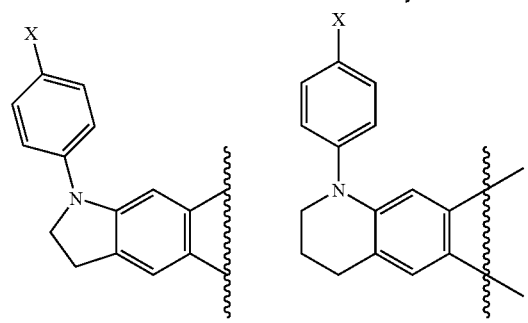

-continued
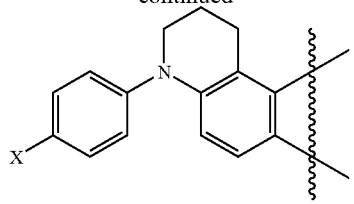
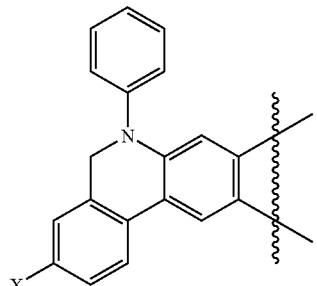
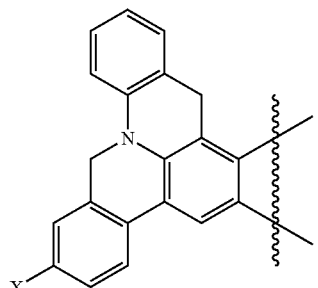
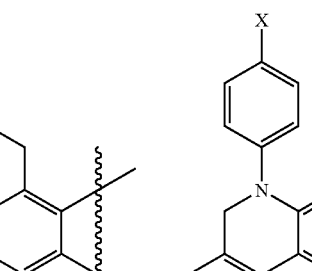
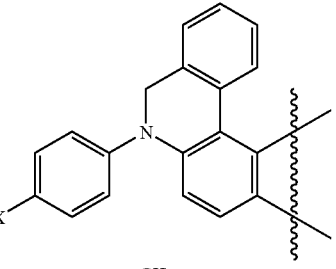
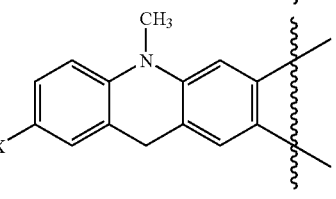
-continued
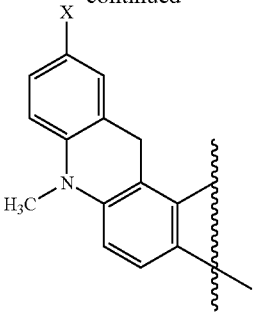
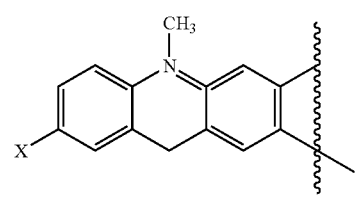
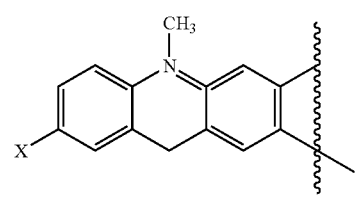
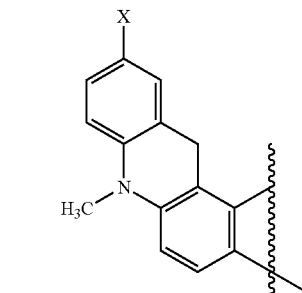
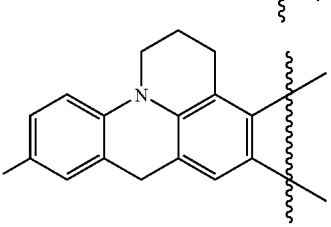
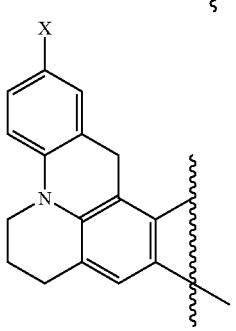
and
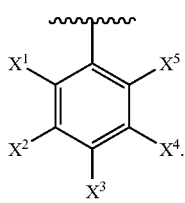
where X is a halogen and R¹ is as defined above.
In one group of embodiments of compounds having formula (I), R⁰ has subformula (a):

In certain instances, $R^0$ is subformula (a), $X^5$ is $CON(R^a)_2$, wherein each $R^a$ is independently selected from H, $(C_1-C_8)$alkyl, hydroxy$(C_1-C_8)$alkyl and protected hydroxy$(C_1-C_8)$alkyl; and one of $X^2$, $X^3$ and $X^4$ is $P^z$. In certain other instances, $R^0$ is subformula (a), $X^5$ in $R^0$ is $CON(R^a)_2$ wherein each $R^a$ is independently selected from H, $(C_1-C_8)$alkyl, hydroxy$(C_1-C_8)$alkyl and protected hydroxy$(C_1-C_8)$alkyl; one of $X^2$, $X^3$ and $X^4$ is $P^z$; and either $A^1$ is O, $A^2$ is OR, or $A^1$ is O and $A^2$ is OR.

Subformulae of Formula (I)

In one embodiment, the present invention provides a fluorescent dye reagent having formula (Ia) or (Ib):

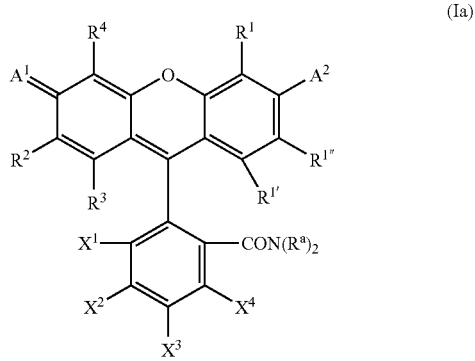

(Ia)

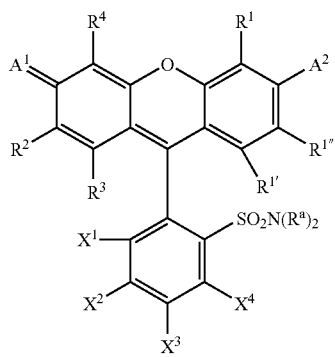

(Ib)

wherein $R^{1'}$, $R^{1'''}$, $R^1$, $R^2$, $R^3$ and $R^4$ are each independently selected from H, halogen, cyano, sulfo, aryl, heteroaryl, $CF_3$, $(C_1-C_8)$alkyl, $(C_1-C_8)$alkylthio, $(C_1-C_8)$alkoxy, $L^f$ and $P^z$, wherein the alkyl portions of any of $R^{1'}$, $R^{1'''}$ and $R^1$ through $R^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms and the aryl or heteroaryl portions of any of $R^{1'}$, $R^{1'''}$ and $R^1$ through $R^4$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^z$; $X^1$ is selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_2N(R^a)_2$ and $CON(R^a)_2$, wherein each $R^a$ is independently selected from H, $(C_1-C_8)$alkyl, hydroxy$(C_1-C_8)$alkyl, protected hydroxy$(C_1-C_8)$alkyl, sulfoalkyl, phosphonoalkyl and alkylphosphonoalkyl, or optionally the two $R^a$ substituents together with the nitrogen atom to which they are attached form a 5- or 6-membered heterocyclic ring having one additional heteroatom selected from O or N; $X^2$, $X^3$ and $X^4$ are each independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, $L^f$ and $P^z$ and optionally, any two adjacent $X^1$ through $X^4$ are combined to form an aromatic or heteroaromatic ring that is optionally further substituted with from one to four substituents selected from halogen cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^z$.

In a second embodiment, the present invention provides a compound of formula (Ic):

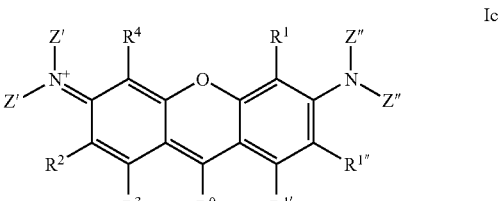

Ic wherein the groups Z' and Z", at each occurrence, are independently selected from the group consisting of hydrogen, $(C_1-C_8)$alkyl, aryl-$(C_1-C_8)$alkyl and aryl, wherein the aliphatic or aryl portions of the Z' or Z" groups are optionally substituted with halogen, $(C_1-C_4)$alkyl, $L^f$ and $P^z$; and optionally the Z' group, at each occurrence is independently combined with $R^2$ or $R^4$ to form a fused 5- or 6-membered saturated or non-saturated ring, and optionally, the Z" group, at each occurrence is independently combined with $R^1$ or $R^{1'''}$ to form a fused 5- or 6-membered ring; wherein if present, said fused 5- or 6-membered saturated or non-saturated ring is optionally fused to an aryl ring and is substituted with halogen, $(C_1-C_4)$alkyl, $L^f$ or $P^z$. In certain instances, $R^0$ is subformula (a) and $X^5$ is $CON(R^a)_2$ wherein each $R^a$ is independently selected from H, $(C_1-C_8)$alkyl, hydroxy$(C_1-C_8)$alkyl and protected hydroxy$(C_1-C_8)$alkyl. In certain other instances, $R^0$ is subformula (a), $X^5$ is $CON(R^a)_2$ wherein each $R^a$ is independently selected from H, $(C_1-C_8)$alkyl, hydroxy$(C_1-C_8)$alkyl and protected hydroxy$(C_1-C_8)$alkyl; and one of $X^2$, $X^3$ and $X^4$ is $P^z$. In yet certain other instances, $R^0$ is subformula (a), $X^5$ is $CON(R^a)_2$ wherein each $R^a$ is independently selected from H, $(C_1-C_8)$alkyl, hydroxy$(C_1-C_8)$alkyl and protected hydroxy$(C_1-C_8)$alkyl; one of $X^2$, $X^3$ and $X^4$ is $P^z$; and each of $R^3$ and $R^{1'}$ are hydrogen.

In certain instances, compounds of formula (Ic) have a structure selected from the group consisting of:
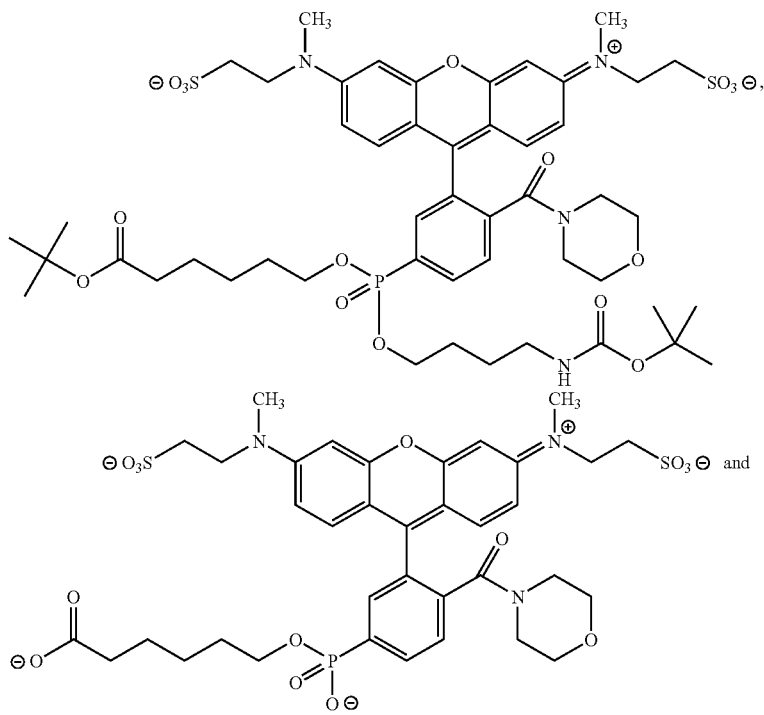
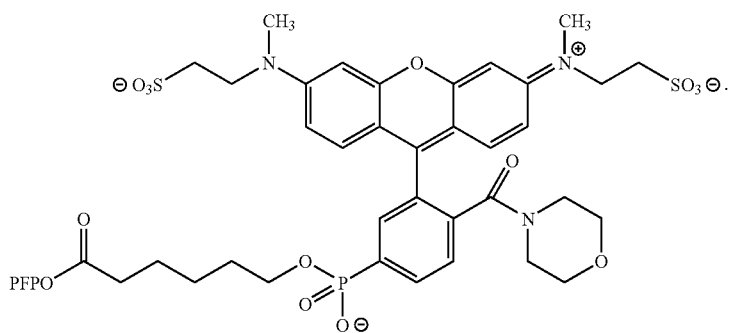
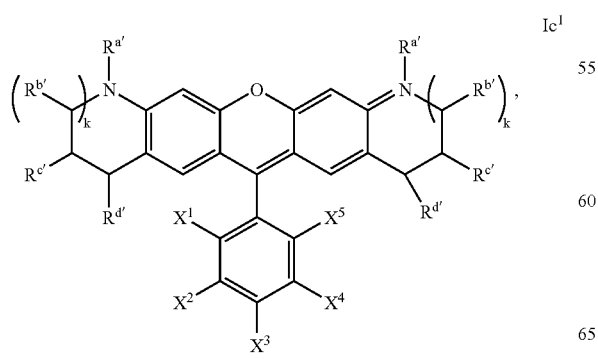
In a third embodiment, the present invention provides a compound selected from the group consisting of:
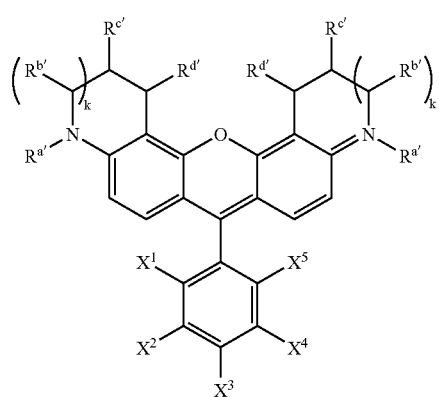

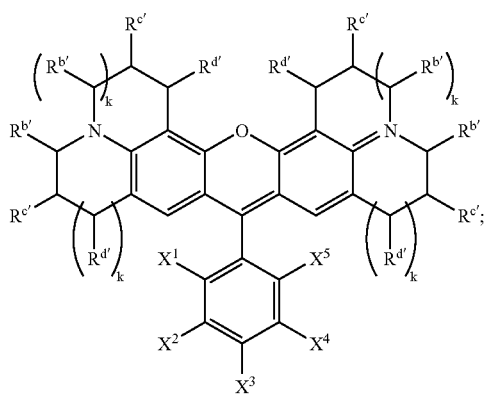

wherein in formulae $Ic^1$-$Ic^3$ each $X^5$ is $CON(R^a)_2$; $R^{a'}$, $R^{b'}$, $R^{c'}$, $R^{d'}$, at each occurrence, is independently selected from the group consisting of hydrogen and $(C_1$-$C_6)$alkyl, or optionally, (i) any of $R^{b'}$, $R^{c'}$ and $R^{d'}$ represents a pair of methyl groups or (ii) any two substituents of $R^{b'}$, $R^{c'}$ and $R^{d'}$, that are attached to adjacent ring atoms are combined to form a fused 6-membered aryl ring, said fused ring is optionally substituted with $P^z$ or $L^f$; and each subscript k is independently an integer from 0-1. In certain instances, one of $X^2$, $X^3$ and $X^4$ is $P^z$. In certain other instances, in compound of formula $(Ic^3)$, each of $R^{b'}$, $R^{c'}$ and $R^{d'}$ is hydrogen. In yet certain other instances, compounds of formulae $Ic^1$-$Ic^3$ have a structure selected from the group consisting of:

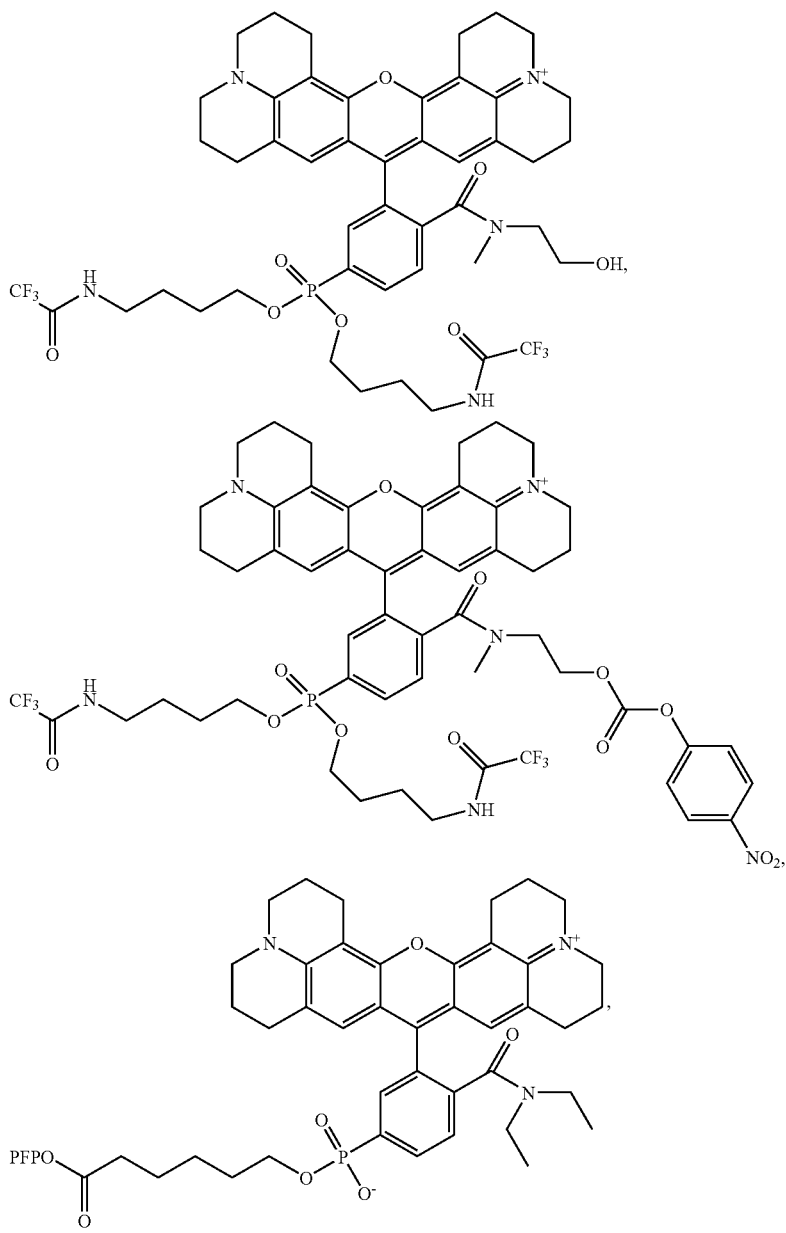

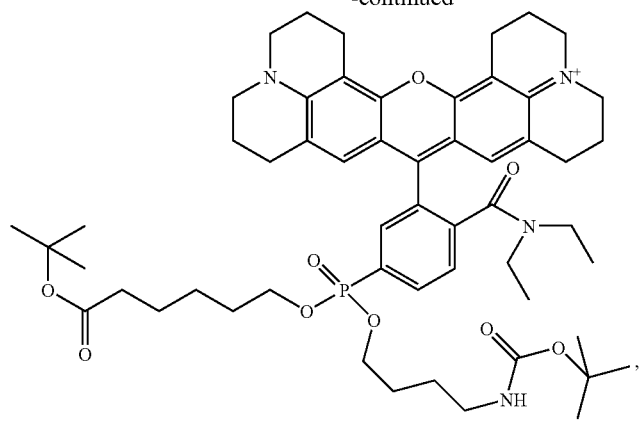
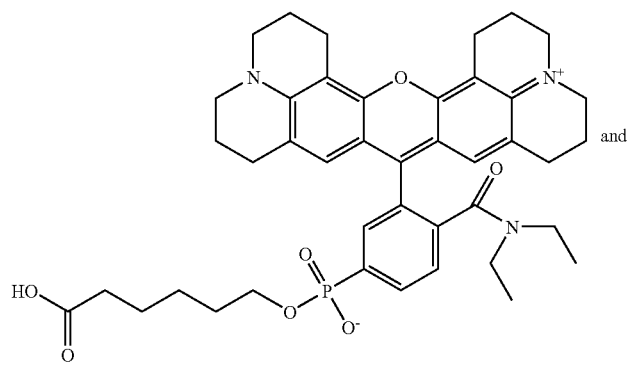
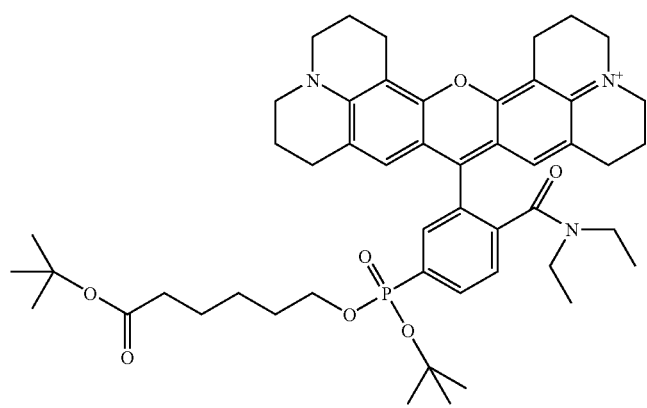

In a related aspect, xanthene dyes having 3-carboxylate or 3-PFP ester substituents are novel intermediates useful in the synthesis of 3-amide substituted xanthene dyes. In some embodiments, 3-carboxylate or 3-PFP ester substituted compounds are selected from the group consisting of:

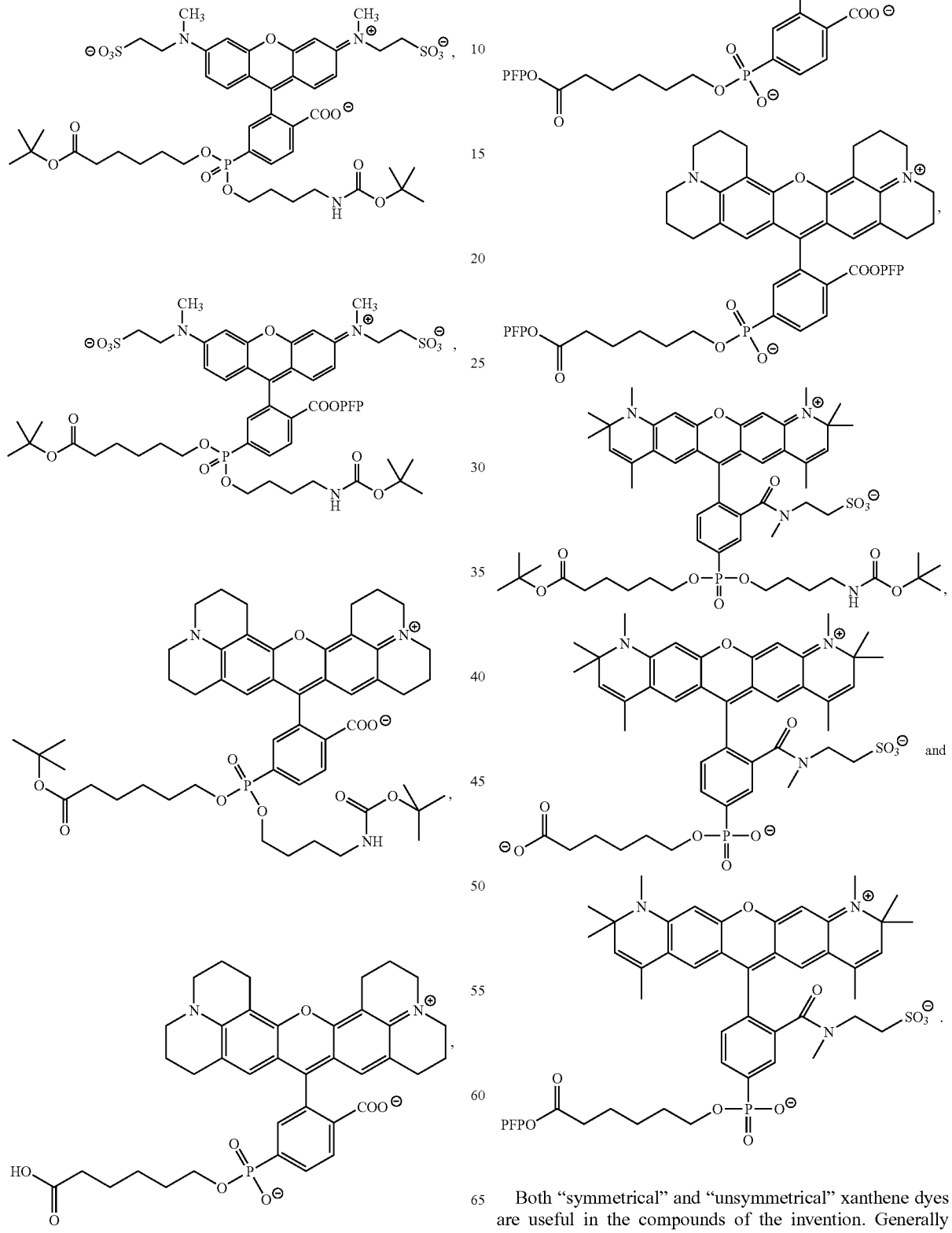

Both "symmetrical" and "unsymmetrical" xanthene dyes are useful in the compounds of the invention. Generally described here, symmetrical xanthenes are readily synthesized following the synthetic route shown below in Scheme A (below) starting from phthalic anhydride and a 3-aminophenol derivative following the synthetic procedures as described in (Color Index, 3rd Edition, Vol. 4: 420 (1971)). Unsymmetrical xanthenes can be synthesized following a similar synthetic route to the one described in FIG. 2 by substituting the carboxylic acid intermediate (Int) formed with compound (s2) an example of a "3-aminophenol".

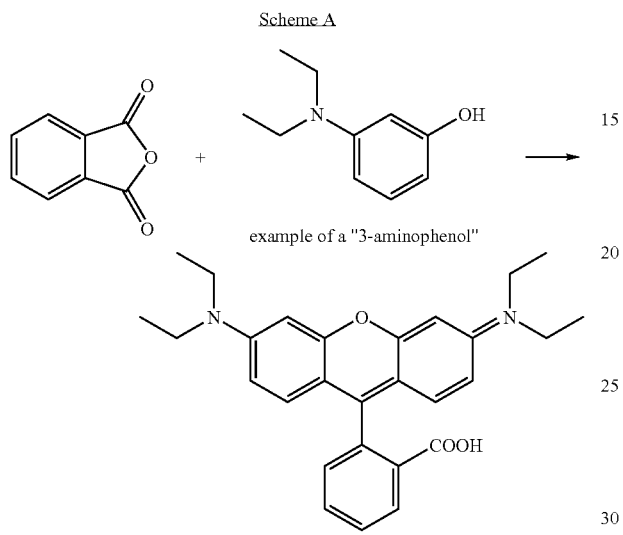

3-Aminophenol analogs are well known in the art. Many are commercially available, or are readily accessible by following the synthetic methods reported in the literature or by methods generally known to a skilled artisan. In one embodiment, the 3-aminophenols that are useful in the synthesis of xanthene dyes components of the invention include, but are not limited to, those set forth in Table IA.

TABLE IA 1. 3-[methyl(phenyl)amino]phenol, 5-methyl-5,6-dihydrophenanthridin-3-ol
2. 5-methyl-5,6-dihydrophenanthridin-1-ol
3. 1-phenylindolin-4-ol, 1-phenylindolin-6-ol
4. 1-phenyl-1,2,3,4-tetrahydroquinolin-7-ol
5. 1-phenyl-1,2,3,4-tetrahydroquinolin-5-ol
6. 5-phenyl-5,6-dihydrophenanthridin-3-ol
7. 5-phenyl-5,6-dihydrophenanthridin-1-ol
8. 2,3,6,7-tetrahydro-1H,5H-pyrido[3,2,1-ij]quinolin-8-ol
9. 8H,13H-12b-Aza-dibenzo[a,de]anthracen-7-ol
10. 8H,9H-8a-Aza-benzo[fg]naphthacen-1-ol
11. 10-methyl-9,10-dihydroacridin-3-ol
12. 10-methyl-9,10-dihydroacridin-1-ol, 2,3-dihydro-1H
13. 7H-pyrido[3,2,10-de]acridin-4-ol
14. 2,3-Dihydro-1H,7H-pyrido[3,2,1-de]acridin-6-ol
15. 9-methyl-9H-carbazol-2-ol and 9-methyl-9H-carbazol-4-ol.

It will be appreciated by those skilled in the art that additional 3-aminophenol derivatives can be prepared from the 3-aminophenols compounds set forth above, that will also be useful for the synthesis of the xanthene dyes of the present invention. For example, other derivatives, (e.g., halogenated derivatives, and derivatives with other substituents, linkers or linking groups having the appropriate reactive groups), can be prepared from the 3-aminophenol compounds set forth in Table IA by methods known in the art and will also be useful synthetic precursors for preparing xanthene dyes. In one illustrative example, the halogenated derivatives of the compounds in Table IA can be prepared by, using known procedures, e.g., nitration, followed by reduction of the nitro compound to the amine, which can be converted to the halogenated analog using the Sandmeyer reaction. A specific group of halogenated 3-aminophenol derivatives that are useful for the synthesis of xanthene dyes are set forth in Table 1B.

TABLE IB

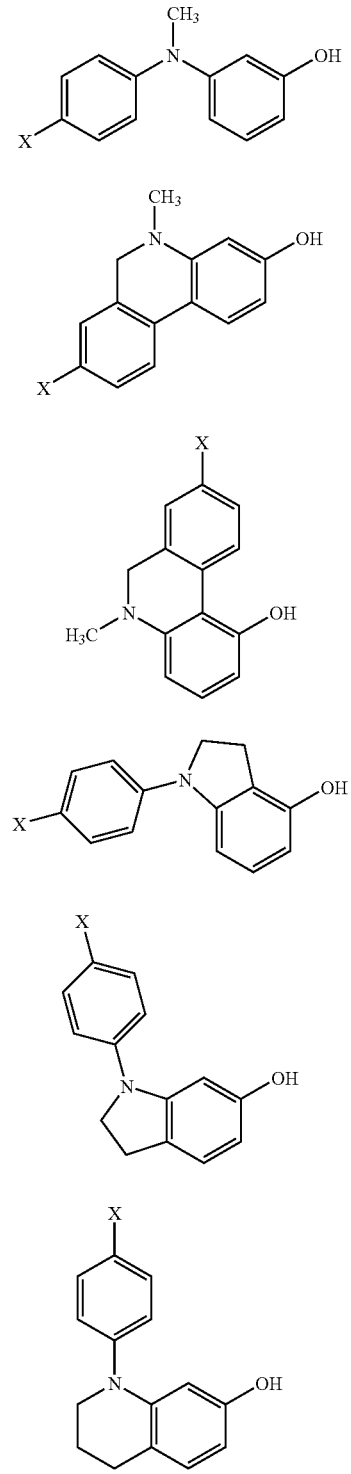

TABLE IB-continued
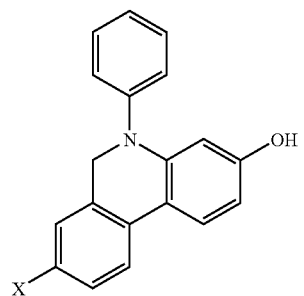
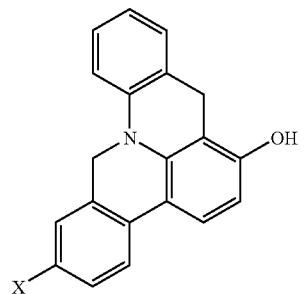
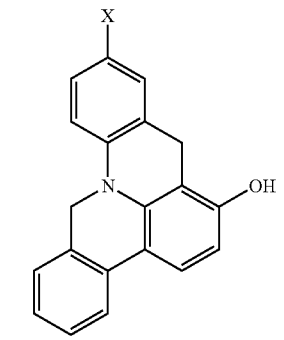
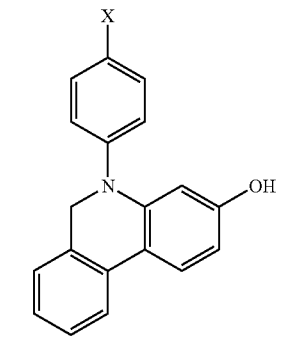
TABLE IB-continued
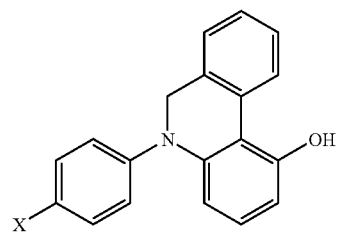
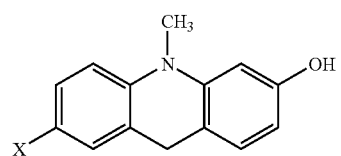
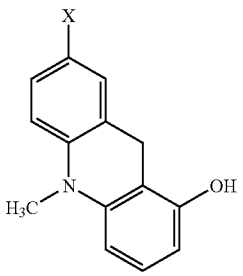
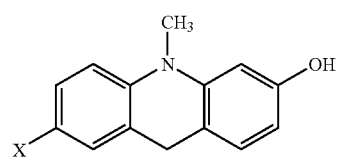
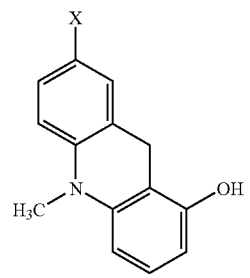
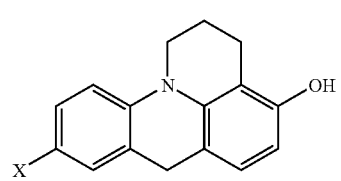
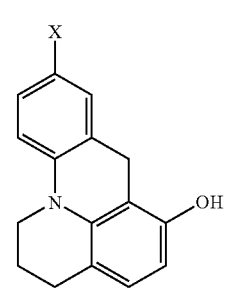
X = halogen It will be appreciated by those skilled in the art that the halogenated 3-aminophenols compounds shown in Table IB can be further reacted with, for example, phthalic anhydride, to form a halogenated xanthene dye component, which can further be reacted with a compound (such as, for example, compound 3 shown in Reaction Scheme 1) using the palladium-mediated synthetic methods described herein, to form xanthene dye components having formula Ic. Additionally, it will be appreciated that additional halogenated 3-aminophenols having a different halogen substitution patterns as well as additional non-halogenated derivatives can be prepared by similar methods.

Additional details concerning the syntheses of compounds having a xanthene dye component is provided in the Examples section of the application.

In one embodiment, the fluorescent dye components are symmetrical xanthene dyes, and in another embodiment, the fluorescent dye components are unsymmetrical xanthene dyes. In one embodiment, the symmetrical or unsymmetrical xanthene dye components are prepared using the 3-aminophenol compounds set forth in Table IB.

General Synthesis of Phosphonylated Dyes

In another aspect, the present invention provides a method of preparing a phosphonylated-fluorescent dye derivative, the method comprising contacting a halo-fluorescent dye substrate having at least one halogen atom attached to an aromatic ring carbon atom, with a phosphite reagent under conditions sufficient to remove the halogen atom and covalently attach a phosphonate group to the aromatic ring carbon atom to form the phosphonylated-fluorescent dye derivative.

In a number of embodiments, the halo-fluorescent dye substrate is selected from halo coumarins, halo benzocoumarins, halo xanthenes, halo benzo[a]xanthenes, halo benzo[b]xanthenes, halo benzo[c]xanthenes, halo cyanines, halo acridines, halo dipyrromethaneboron difluorides, halo phenoxazines, halo benzo[a]phenoxazines, halo benzo[b]phenoxazines and halo benzo[c]phenoxazines.

The present invention provides a compound having the formula:

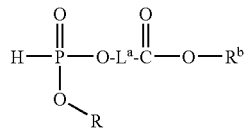

wherein $L^a$ is a member selected from the group consisting of a $(C_4$-$C_{20})$alkylene linking group; $R^b$ is selected from the group consisting of t-butyl, tetrahydofuranyl, tetrahydrpyranyl, pentafluorophenyl and trialkylsilyl; and R is a labile protecting group selected from t-butyl, —$CH_2CH_2CN$, —$CH_2CH_2TMS$, —$(CH_2)_4NHC(O)OR^b$ and a phosphate protecting group. Non-limiting exemplary phosphate protecting groups include trihaloalkyl, benzyl, nitrobenzyl, chlorobenzyl, fluorenyl-9-methyl. In some embodiments, $L^a$ is $C_5$-alkylene, such as —$(CH_2)_5$— and $R^b$ is t-butyl, tetrahydofuranyl, tetrahydrpyranyl, pentafluorophenyl and trialkylsilyl. In one instance, $R^b$ is t-Butyl. In certain other embodiments, $L^a$ is $C_5$-alkylene and R is t-butyl, —$CH_2CH_2CN$, —$CH_2CH_2TMS$ or —$(CH_2)_4NHC(O)OR^b$. In yet some embodiments, $L^a$ is —$(CH_2)_5$— and R is t-butyl, —$CH_2CH_2CN$, —$CH_2CH_2TMS$, —$(CH_2)_4NHC(O)OR^b$ and a phosphate protecting group. In certain instances, R is —$(CH_2)_4NHC(O)OR^b$ or t-butyl. In one occurrence, $R^b$ is t-butyl. In some preferred embodiments, the compound is selected from:

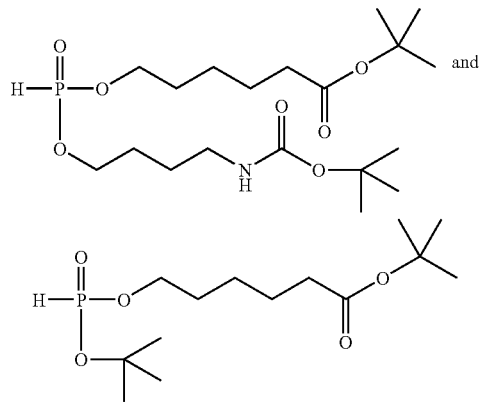

While the above structures are provided in a single tautomeric form, one of skill in the art will appreciate the recitation is further meant to include all forms, including the commonly used trivalent phosphite form.

General Procedures for the Preparation of Amide-Substituted Dyes

The xanthene dyes of the present invention can be prepared following the Reaction Schemes outlined below and in FIGS. 1-9.

Reaction Scheme 1A illustrates a general procedure for the synthesis of an unsymmetric phosphonate reagent.

Reaction Scheme 1A

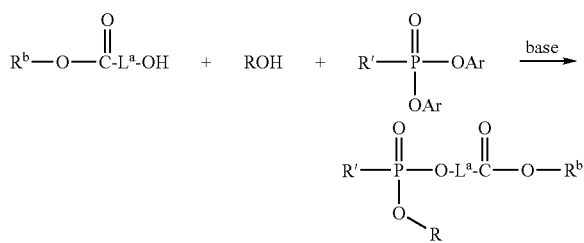

where R' is hydrogen, alkyl, or aryl. R' is preferably —H. Ar is aryl. Preferably Ar is phenyl. The base is preferably an organic base, such as pyridine or an amine. $L^a$ is a $(C_4$-$C_{20})$ alkylene linking group, preferably a $C_5$-alkylene. $R^b$ is selected from the group consisting of t-butyl, tetrahydrofuranyl, tetrahydropyranyl, pentafluorophenyl and trialkylsilyl. R is a labile protecting group selected from t-butyl, —$CH_2CH_2CN$, —$CH_2CH_2TMS$ and —$(CH_2)_4NHC(O)OR^b$.

Reaction Scheme 1 (FIG. 1) illustrates the synthesis of an unsymmetric phosphonate reagent tert-butyl 6-{[oxido(3'-{(tert-butoxycarbonyl)-amino}butyl)phosphino]oxy}hexanoate (3).

A mixture of tert-butyl 6-hydroxyhexanoate (1) was reacted with tert-butyl 4-hydroxybutylcarbamate (2) in the presence of diphenylphosphite and pyridine to yield the desired unsymmetric phosphate, tert-butyl 6-{[oxido(3'-{(tert-butoxycarbonyl)amino}butyl)phosphino]oxy}hexanoate (3) after chromatographic separation. The symmetric phosphite reagent bis(4-(2,2,2-trifluoroacetamido)butyl)phosphate (4), shown below, has been disclosed in U.S. patent application No. 2006/0199955.

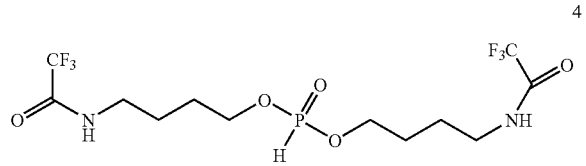

Figure 2:
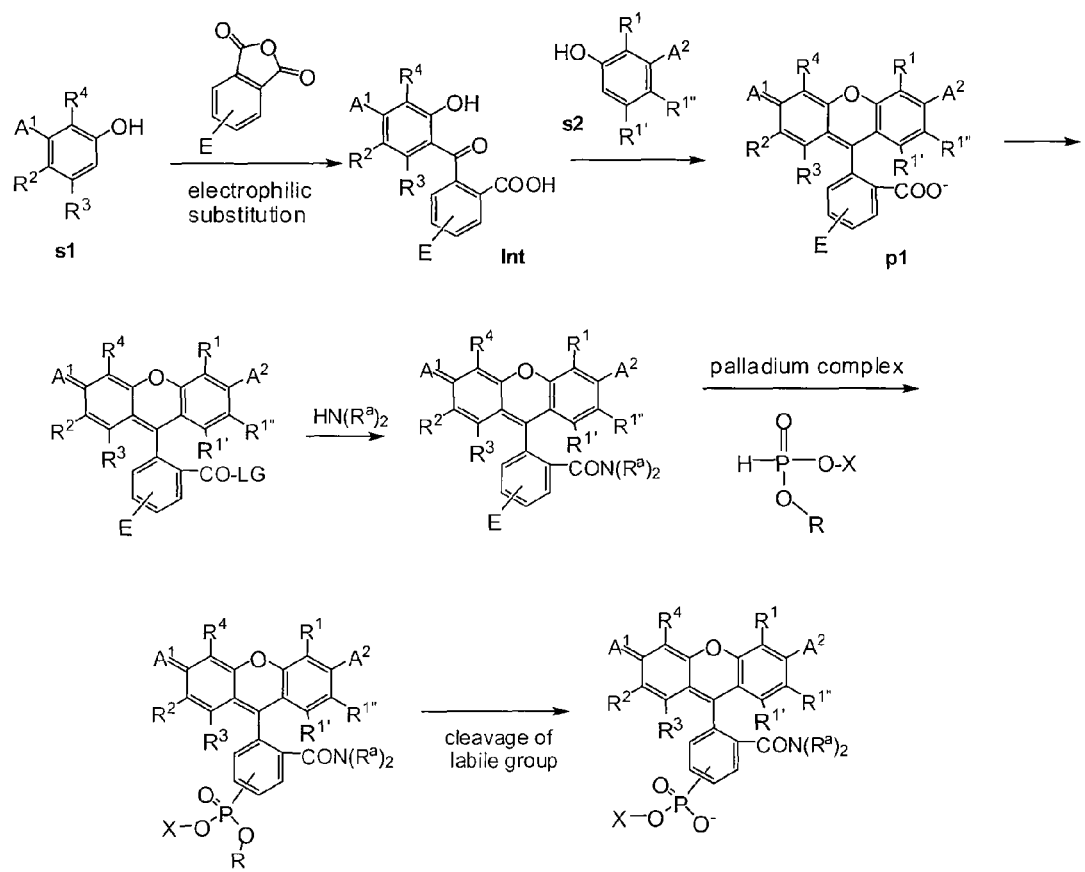
FIG. 2 illustrates a general synthetic approach to certain xanthene fluorescent dye reagents of the present invention.
Figure 3:
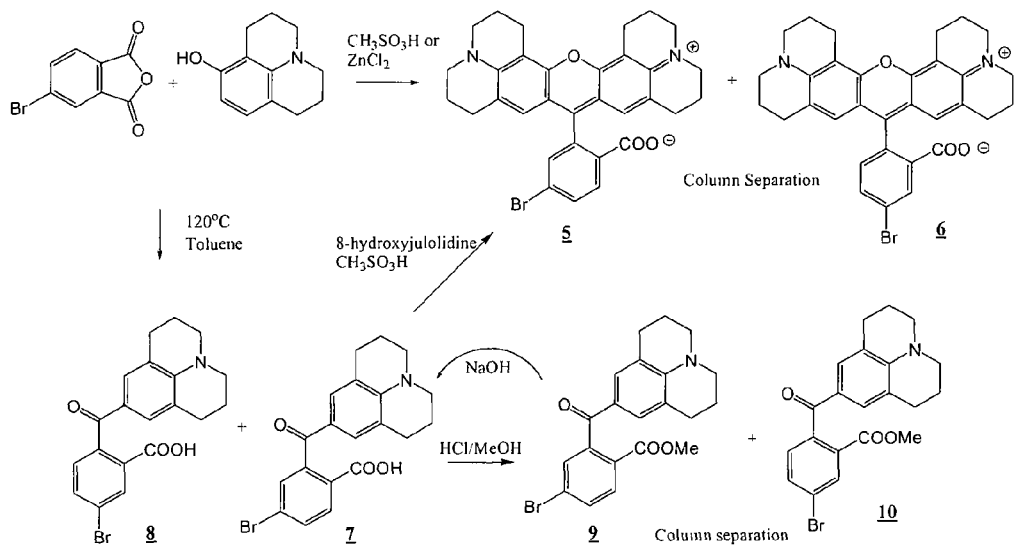
FIG. 3 illustrates a synthetic route to isomerically pure 5-bromo-substituted benzophenone dyes that can be converted to carboxamide dyes of the present invention.
Figure 4:
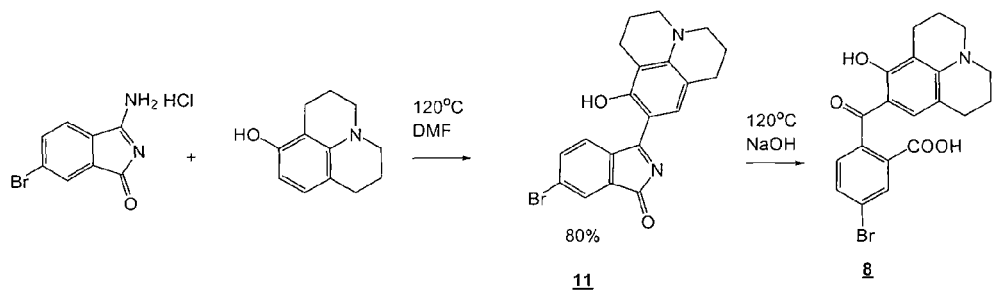
FIG. 4 shows a new regiospecific synthesis of bromo-substituted benzophenone dye intermediates.
Figure 5:
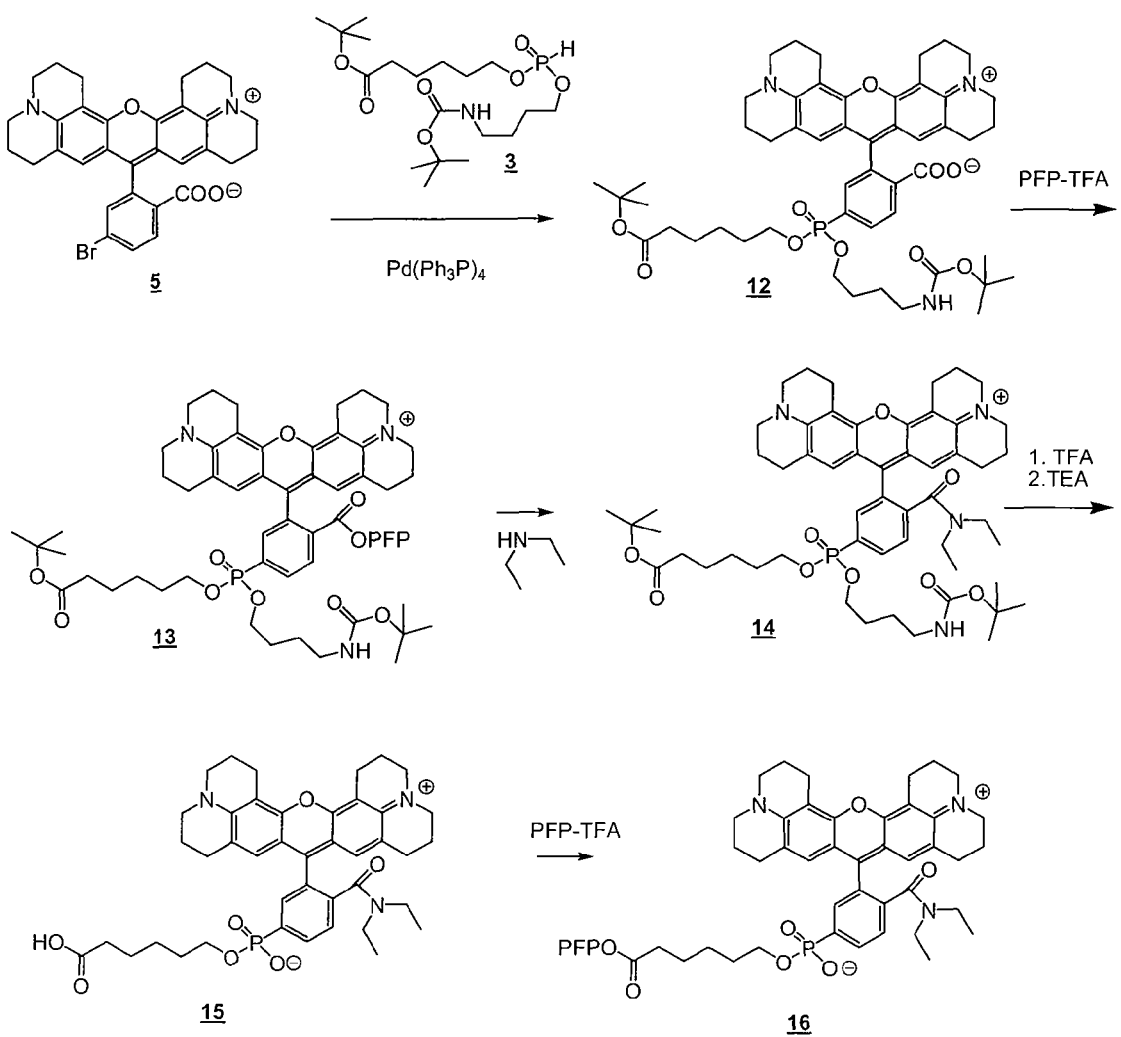
FIG. 5 illustrates the synthesis of two substituted carboxamide phosphonylated rhodamine analogs (compounds 15 and 16).
Figure 6:
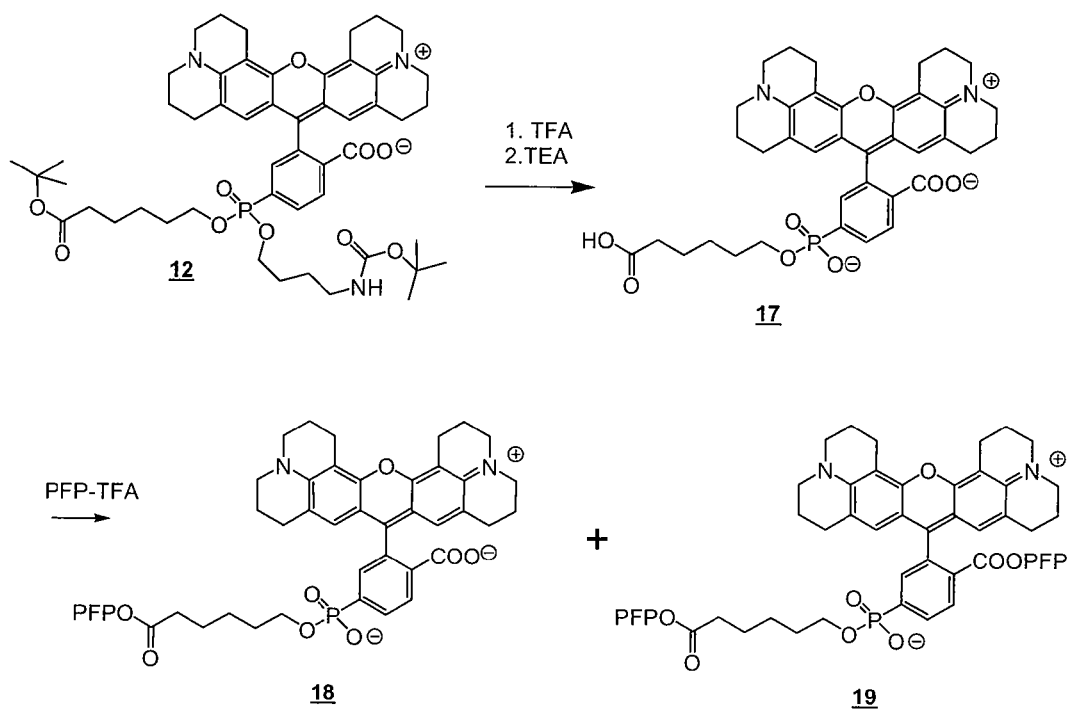
FIG. 6 illustrates preparation of a non-carboxamido rhodamine dye and its PFP activated ester.
Figure 7:
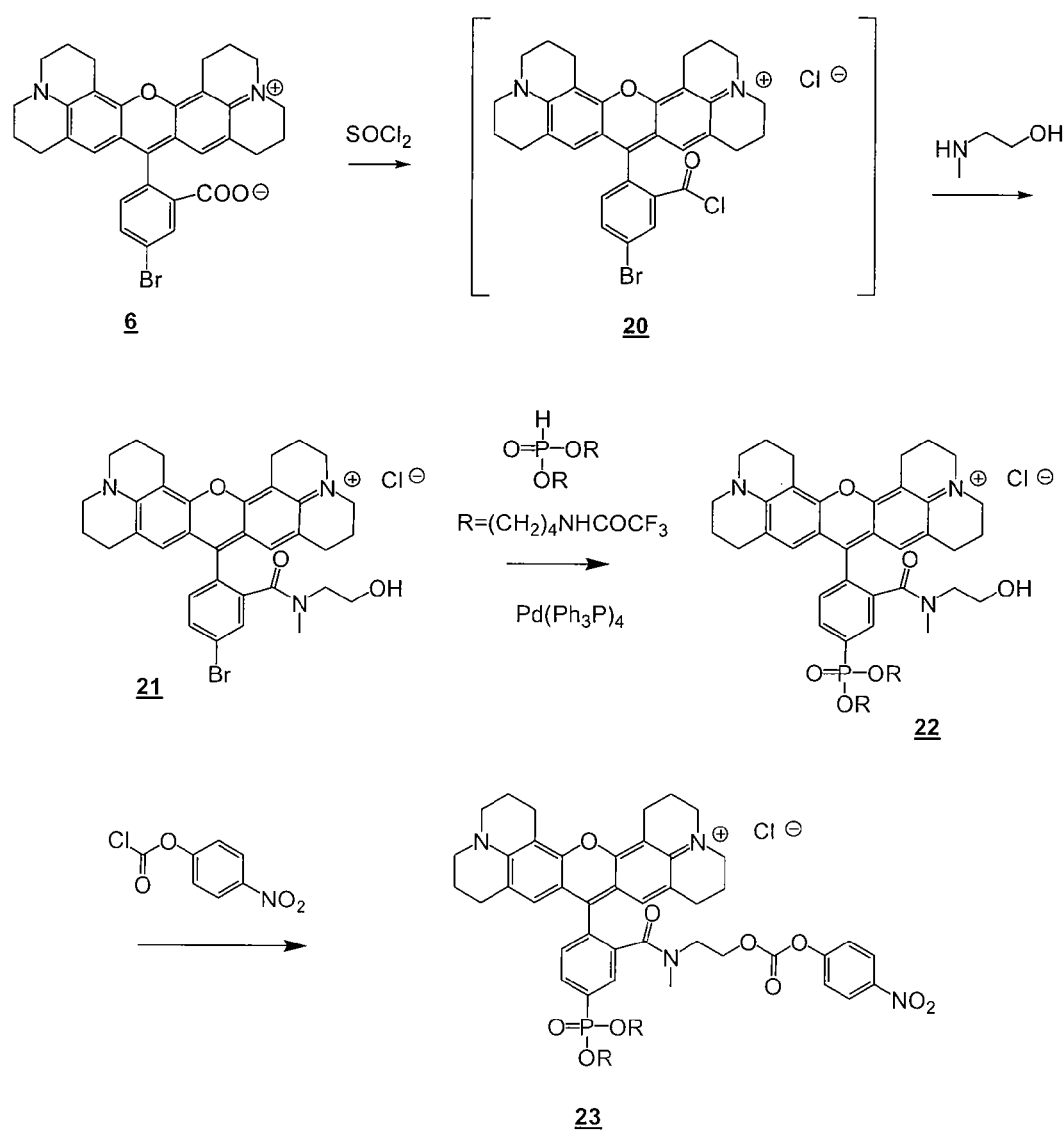
FIG. 7 illustrates the synthesis of two phosphonylated 3-carboxamide-substituted rhodamine dyes (compounds 22 and 23) from a pure rhodamine isomer.
Figure 8:
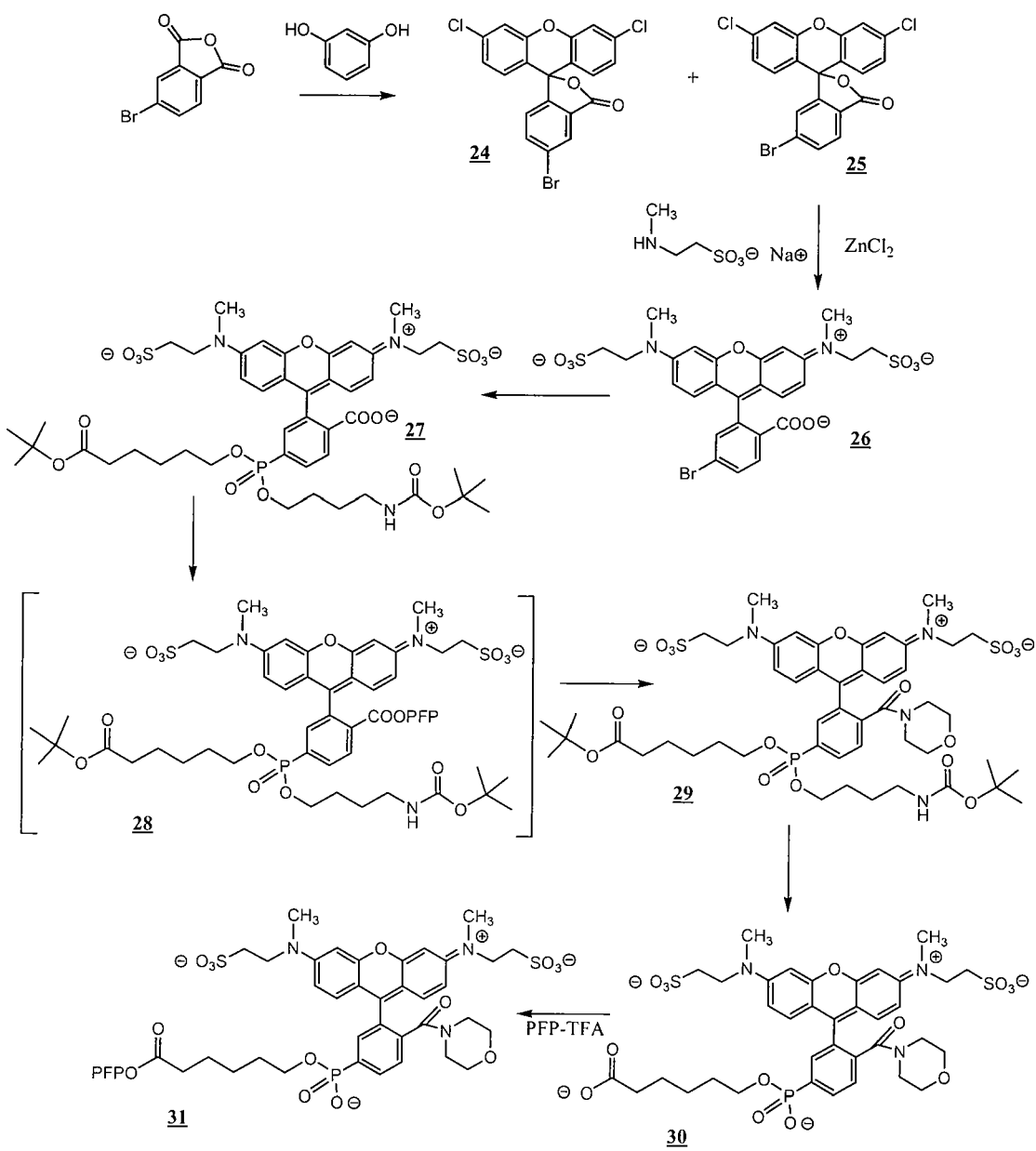
FIG. 8 illustrates the synthesis of a phosphonylated 3-carboxamide-substituted rhodamine dye having sulfonate groups.

According to an embodiment of the present invention, FIG. 2 outlines a general synthetic approach to certain xanthene fluorescent dye reagents of the present invention. where E is halogen, such as Cl or Br, LG is a labile group or a leaving group. Examples of LG include, but are not limited to, —Cl, Br, —O-aryl, such as —OPh. X is -L—$N^a$, -L—$NR^AR^B$ or $L^f$. Substituents L, $N^a$, $R^A$ and $R^B$ and other substituents are as defined above. In FIG. 2, phenol starting material s1 is reacted with an anhydride to form an intermediate Int, which is further reacted with another phenol s2 to form xanthene precursor p1. Subsequent reactions of p1 in the sequence shown in FIG. 2 produce final 3-amide substituted phosphonylated xanthenes.

Reaction Schemes 2 and 3 (FIGS. 3 and 4) illustrate two synthetic approaches to produce isomerically pure bromo-substituted dyes or benzophenone intermediates.

As shown in Reaction Scheme 2 (FIG. 3) the commonly used procedures give rise 6- and 5-dye isomers (compounds 5 and 6) which require tedious chromatographic separation. Alternatively, 8-hydroxyjulolidine and 4-bromophthalic anhydride is converted to the isomeric mixture of benzophenones 7 and 8. The mixture was converted to the methyl ester derivatives 9 and 10 which were separated by silica gel chromatography. The methyl ester of 9 was hydrolyzed under alkaline conditions to yield the pure isomer 7 which was then converted to pure 6-bromosubstituted dye 5. These procedures lead to relatively low yields of the pure dyes and increased cost related to the chromatography separation.

Reaction Scheme 3 (FIG. 4) shows a regiospecific synthesis of bromo-substituted benzophenone dyes, which eliminates the separation of isomers by chromatography. 3-Amino-6-bromo-1H-isoindol-1-one hydrochloride (U.S. Pat. No. 4,900,739) and 8-hydroxyjulolidine was heated at 120° C. in DMF to yield substituted 6-bromo-1H-isoindol-1-one 11 which was converted in NaOH at 120° C. to the isomerically pure benzophenone 8. This isomer can be converted as shown in Reaction Scheme 2 to the desired 5-bromo-substituted rhodamine dye 6 intermediate, which can be converted to other rhodamine dyes or isomeric equivalents.

Similarly starting from 3-amino-5-bromo-1H-isoindol-1-one hydrochloride the 5-bromo-substituted rhodamine dye 5 can be prepared.

Reaction Scheme 4 (FIG. 5) illustrates the synthesis of the substituted carboxamide phosphonylated rhodamine analog 16.

Rhodamine dye 5 was converted into phosphonylated dye 12 using phosphite 3 in the presence of tetrakis(triphenylphosphine)palladium(0) catalyst. Intermediate 12 was first reacted with activated with pentafluorophenyl trifluoroacetate (PFP-TFA) to yield the PFP-ester 13, which was converted to the N,N'-diethylcarboxamide 14 by reaction with diethylamine. Deprotection by treatment first with trifluoroacetic acid then followed by reaction with triethylamine yielded the 5-carboxypentyl phosphonate 15. This intermediate was converted the PFP ester of the desired substituted carboxamide phosphonylated rhodamine analog 16. In one embodiment, 6-bromorhodamine analog was prepared by reacting 8-Hydroxyjulolidine and 5-bromoisobenzofuran-1,3-dione in the presence of propionic acid and methylsulfonic acid.

Reaction scheme 5 (FIG. 6) illustrates preparation of a non-carboxamido rhodamine dye and its PFP activated ester (18).

Selective activation of the aliphatic carboxy-group of the phosphonate moiety in compound 17 is complicated by a competing reaction of the aromatic carboxy group (compound 19).

Reaction Scheme 6 (FIG. 7) illustrates the synthesis of another phosphonylated 3-carboxamide-substituted rhodamine dye 23.

As shown in reaction scheme 6, rhodamine dye 6 was converted into acid chloride 20 using thionyl chloride which was reacted without isolation with N-methyl-2-aminoethanol to afford carboxamide 21. Phosphonylation of 21 with reagent 4 in the presence of the palladium(0) catalyst gave the phosphonate 22, which was then converted to the activated p-nitrophenyl carbonate dye 23.

Reaction Scheme 7 (FIG. 8) illustrates the synthesis of another phosphonylated 3-carboxamide-substituted rhodamine dye 31.

An isomeric mixture of 5/6-bromofluorescein dichloride was prepared by a reaction of 4-bromophthalic anhydride and resorcinol in the presence of $POCl_3$. Chromatographic separation gave pure isomers 24 and 25. Isomer 25 was reacted with N-methyl taurine in the presence of zinc chloride to afford bromo-substituted rhodamine dye 26. Palladium catalyzed phosphonylation using phosphite 3 yielded phosphonate-substituted dye 27. 3-Carboxy group of 27 was converted into PFP ester by treatment with PFP-TFA. The resultant PFP ester 28 was reacted with morpholine to give 3-carboxamide 29. Fully protected phosphonate was converted into hexanoyl phosphonate 30 by treatment first with TFA and second with TEA. Final activation of the carboxy group using PFP-TFA afforded PFP-ester 31.

Carboxamide-substituted phosphonylated fluoresceine-type dyes can be prepared from a common xanthene dye. In certain instances, the approach utilizes the methods described in this invention and those disclosed in WO 2005/102176 starting with any 5- or 6-bromo-substituted xanthene dye, which can be converted to a carboxamide-substituted phosphonylated fluoresceine-type dye.

Figure 9:
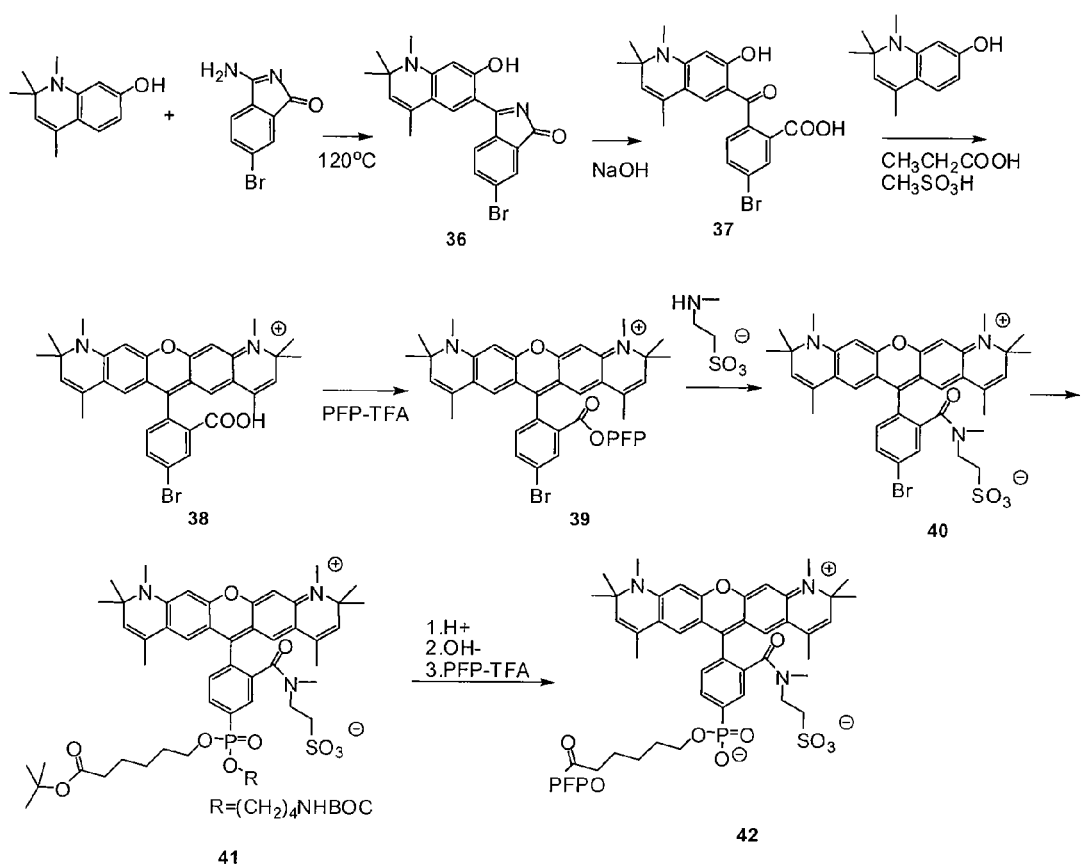
FIG. 9 illustrates the synthesis of a phosphonylated rhodamine dye having a sulfonated 3-carboxamide group.

FIG. 9 illustrates a synthetic route for the preparation of a phosphonylated rhodamine-type dye having a sulfonate group at the 3-carboxamide substituent.

Figure 10:
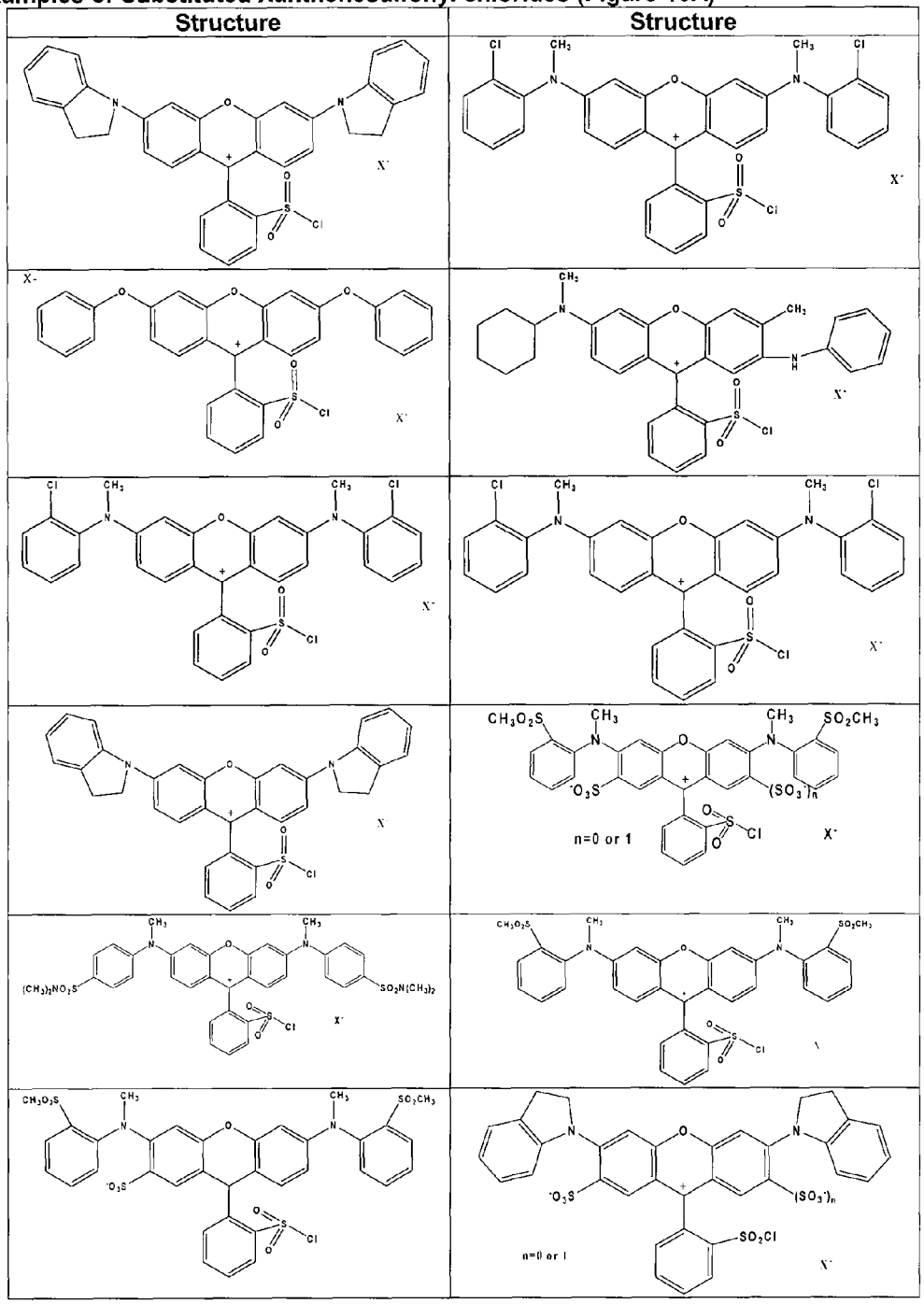
FIG. 10 provides the structures of various known sulfonylated xanthene dyes.
Figure 10:
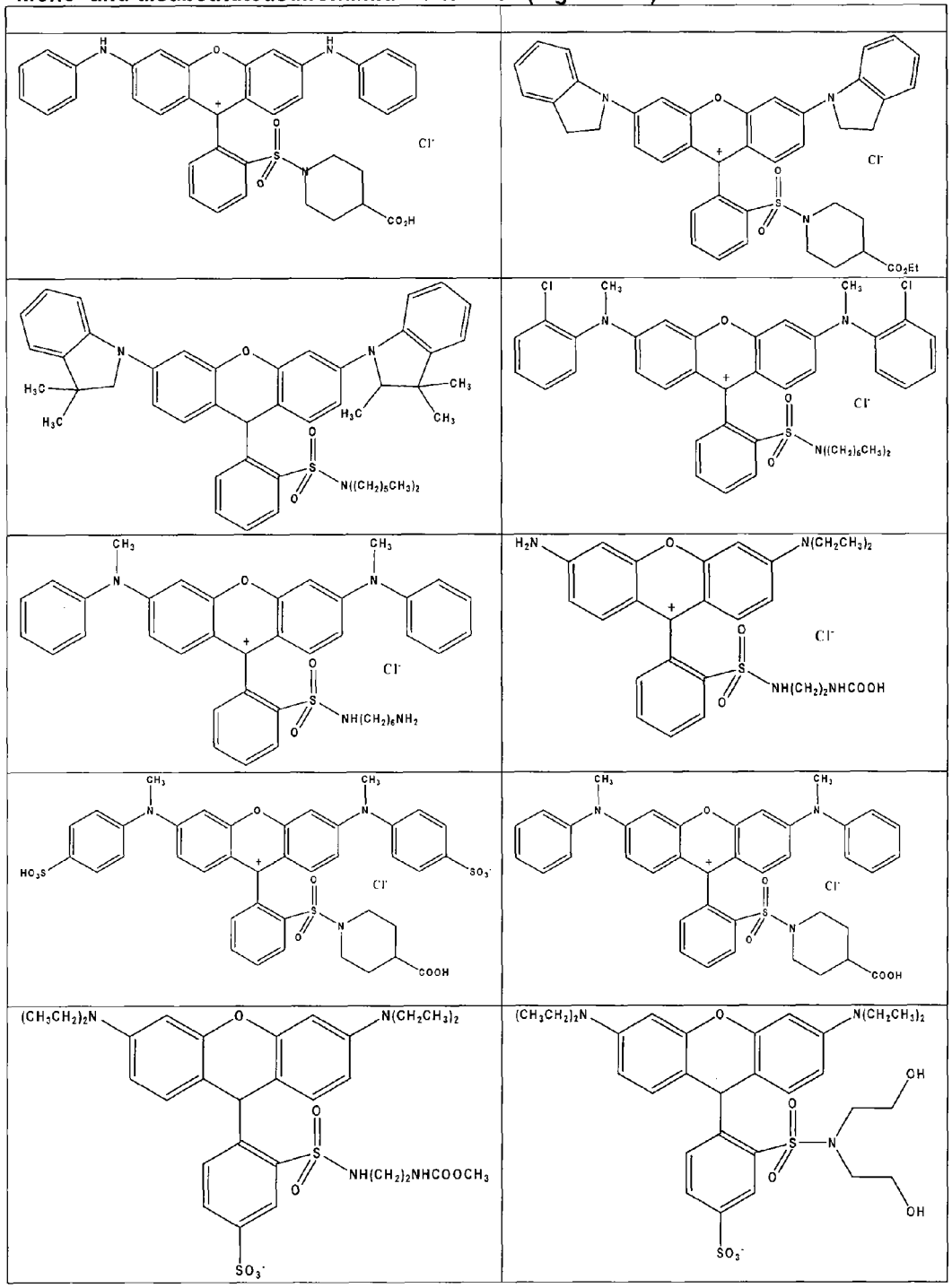

The preparation of sulfonamide compounds (Formula Ib) can be accomplished using similar methods and intermediates to those provided above. In general, the sulfonamide compounds of the present invention can be prepared from derivatives having a sulfonyl chloride substituent at the $X^1$ or $X^5$ position of Formula I. The sulfonyl chloride can be prepared from a precursor sulfonic acid. A number of methods are known for the general preparation of sulforhodamine, sulfoxanthene and sulfonamidoxanthenes (see, Corrie et al, *Bioconjugate Chemistry*, 12:186-194 (2001), EP 0174054, U.S. Pat. No. 4,405,788, WO 9113122 and US 20060230545. FIG. 10 provides structures of sulfo and sulfonamide dyes prepared in the noted references.

Those skilled in the art will appreciate that all the xanthene dye examples shown in Reaction Schemes 2 to 8 can contain different linking chains and additional substitutions which may include one or more rings.

Still further, combining methods disclosed for the preparation of non-phosphonylated 3-amidophenyl-xanthenes (see U.S. Pat. Nos. 4,647,675; 6,399,392;U.S. Patent Application No. 2006/0154251, as well as PCT publications WO 2002/055512 and WO 2005/102176) with the methods and know-how disclosed herein as well as previously filed U.S. patent application Ser. Nos. 11/202,635 and 11/360,040, allows the synthesis of phosphonylated 3-amidophenyl fluorescein- and 3-amidophenyl rhodol-based xanthenes. All of these references are hereby incorporated by reference.

Oligonucleotide Probes and other Labeled Biological Agents

In another aspect, the present invention provides oligonucleotide probes and other biological agents in which one or more of the fluorescent dyes above have been attached to a nucleic acid, polynucleotide, oligonucleotide and the like. As noted above, the present invention finds broad application in labeling of nucleic acids (including nucleotides, nucleosides, DNA, RNA, PNA, locked nucleic acids, oligonucleotides and the like), peptides or proteins, oligosaccharides, glycosylated proteins, and other biological agents. Additionally, the nucleic acids can include modified bases (e.g., 5-substituted pyrimidines, 3-substituted purines, substituted deazapurines, substituted pyrazolo[3,4-d]pyrimidines, and the like). See, for example, U.S. Pat. Nos. 6,660,845 and 7,045,610. The invention also finds utility in labeling of oligonucleotides and modified oligonucleotides having attached groups such as minor groove binders, quenching agents or quenchers, intercalators, crosslinking groups, and the like.

In one embodiment of the invention, the phosphonate dyes contain at least one group -L-$R^X$ where $R^X$ is the reactive group that is attached to the fluorophore by a covalent linkage L. In certain embodiments, the covalent linkage attaching the phosphonate dye to $R^X$ contains multiple intervening atoms that serve as a spacer. The dyes with a reactive $R^X$ group fluorescently label a wide variety of organic or inorganic substances that contain or are modified to contain functional groups with suitable reactivity, resulting in chemical attachment of the conjugated substance ($R^Y$), represented by -L-$R^Y$. The reactive group and functional group are typically an electrophile and a nucleophile that can generate a covalent linkage. Typically, the conjugation reaction between the reactive dye and the substance to be conjugated results in one or more atoms of the reactive group $R^X$ to be incorporated into a new linkage L attaching the phosphonate dye to the conjugated substance $R^Y$.

Selected examples of functional groups involved to form linkages where the reaction of an electrophilic group and a nucleophilic group yields a covalent linkage are shown below.

Examples of nucleophilic groups include —$NH_2$, —$NHNH_2$, —$ONH_2$, —NHC=(O)$NHNH_2$, —OH, —COOH, or —SH. The electrophilic groups are activated esters, acrylamides, acyl azides, acyl halides, aldehyde or ketones, alkyl halides, alkyl sulfonates, anhydrides, aryl halides, aziridines, boranates, carboxylic acids, carbodiimides, diazoalkanes, epoxides, haloacetamides, halotriazines, imidoesters, isocyanates, isothiocyanates, maleimides, phophoramidites, silyl halides, sulfonate ester and sulfonyl halides. Additionally, a spacer can include hetero atoms in linear or acyclic portions, cyclic portions, aromatic rings or combinations thereof.

Conjugated substances include nucleic acids, oligonucleotides, oligonucleotide conjugates, proteins, peptides, drugs, immunoglobulins, receptors, toxins, organic small molecule ligands, enzyme substrates, vitamins, carbohydrates, oligosaccharides, polysaccharides, biotin, streptavidin, solid substrate, and a solid support for oligonucleotide synthesis) described and used herein.

In one embodiment, conjugates of biological polymers such as peptides, proteins, oligonucleotides, nucleic acid polymers are also labeled with a second fluorescent or non-fluorescent dye, including an additional dye of the present invention, to form an energy-transfer pair.

In yet another embodiment, conjugates of biological polymers such as peptides, proteins, oligonucleotides, nucleic acid polymers are also labeled with a second fluorescent or non-fluorescent dye, in addition to the dye of the present invention, to form an energy-transfer pair where the fluorescence of the latter is quenched. In some instances, binding of these conjugated to their natural receptor or complement result in conformational change or cleavage of bond with an increase in fluorescence. Preferred selected examples of dual labeled oligonucleotide probes are 5'-$(MB)_n^y$-$Fl^A$-oligonucleotide-$Fl^B$-3',5'-$Fl^A$-oligonucleotide-$Fl^B$-MB-3' where $Fl^A$ and $Fl^B$ are either a fluorophore or a quencher with the proviso that a probe can contain only one quencher and one fluorophore, MB is a minor groove binder and $n^y$ is 0 or 1. In one embodiment the quencher is non-fluorescent.

In a related embodiment the preferred conjugate probes are used in amplification methods to detect nucleic acid targets, nucleic acid polymorphisms and gene expression analysis. These methods are disclosed in U.S. Pat. No. 6,312,894, WO 2004/018626, Livak, K J and Schmittgen, T D. *Methods* 25: 402-408 (2001).)

Examples of minor groove binders are disclosed U.S. Pat. No. 5,801,155 and quenchers in U.S. Pat. No. 6,699,975 and WO02099141 all which are included by reference in their entireties.

In another embodiment, the conjugated substance is a nucleic acid base, nucleoside, nucleotide or a nucleic acid polymer, including those that were modified to possess an additional linker or spacer for attachment of the dyes of the invention, such as an alkynyl linkage (U.S. Pat. No. 5,047,519; U.S. Pat. No. RE 38,416), an aminoallyl linkage (U.S. Pat. No. 4,711,955) or other linkage.

In one embodiment a xanthenephosphonate ($X^P$) is attached to a solid support through a cleavable linker. The linker molecule also contains a hydroxyl group protected with DMTr (or like) blocking group. After removal of the DMTr group, an oligonucleotide is synthesized on an automated oligonucleotide synthesizer by step-wise attachment of nucleotide units to the hydroxyl group. A quencher is introduced at the 5'-end with the appropriate phosphoramidite, or post-synthetically with a quencher containing a reactive group, to yield an oligodeoxynucleotide (ODN) having an attached xanthenephosphonate moiety ($X^P$) and a quencher (Q). A solid support compatible with oligonucleotide synthesis includes controlled pore glass, polystyrene, plastic, nylon, gold and the like.

In one embodiment a quencher is attached to a solid support through a cleavable linker. The linker molecule also contains a hydroxyl group protected with DMTr (4,4'-dimethoxytrityl) (or like) blocking group. After removal of the DMTr group, an oligonucleotide is synthesized on an automated oligonucleotide synthesizer by step-wise attachment of nucleotide units to the hydroxyl group. A $X^P$ fluorophore is introduced at the 3'-end with the appropriate phosphoramidite, or post-synthetically with a $X^P$ fluorophore containing a reactive group, to yield an ODN having an attached quencher (Q) and $X^P$ moiety. Alternatively, in addition to the $X^P$ and a quencher (Q) a MB is introduced to yield a MB-Q-ODN-L-Fl conjugate. In this connection it is noted that the synthesis of MBs and their attachment to ODNs is well known (see for example U.S. Pat. Nos. 5,801,155, 5,912,340 and 6,084,102; all of which are expressly incorporated herein by reference).

EXAMPLES

General Experimental

All air and water sensitive reactions were carried out under a slight positive pressure of argon. Anhydrous solvents were obtained from Aldrich (Milwaukee, Wis.). Flash chromatography was performed on 230-400 mesh silica gel. $^1$H NMR spectra were run at 20° C. on a Varian 300 spectrophotometer; chemical shifts are reported in ppm downfield from Me$_4$Si. Thin-layer chromatography was run on silica gel 60 F-254 (EM Reagents) aluminum-backed plates.

In the examples below, compound numbering refers to those numbers provided in Reaction Schemes 1-8 (see, FIGS. 1 and 3-9).

Example 1

Preparation of tert-Butyl 6-{[oxido(3'-{(tert-butoxycarbonyl)amino}butyl)phosphino]oxy}hexanoate (3)

This example demonstrates the synthesis of the novel phosphonylation reagent 3 as shown in Reaction Scheme 1.

To a solution of tert-butyl 6-hydroxyhexanoate (1) (J. Org. Chem. (1984), 49(12), 2147) (2.6 g, 13.7 mmol) and tert-butyl 4-hydroxybutylcarbamate (2) (J. Med. Chem. (2006), 49(14), 4183-4195) (2.6 g, 13.7 mmol) in 20 mL of anhydrous pyridine (20 mL) was added 3.1 mL of diphenylphosphite (85% pure). After being stirred at room temperature overnight, the reaction was concentrated and re-dissolved in ethyl acetate. The solution was washed with 10% citric acid, saturated NaCl and dried over Na$_2$SO$_4$. The crude material obtained after solvent evaporation was chromatographed on silica eluting first with 1:1 ethyl acetate:hexane to separate phenol and one of the symmetric by-products and, second, with ethyl acetate to elute the desired phosphite 3. Concentration of the pure product fractions gave 2.05 g of the phosphite 3 as a viscous liquid. H$^1$-NMR (DMSO-d6): δ 6.92 (br t, NH, 1H), 6.80 (d, J=692 Hz, PH, 1H), 3.97 (m, 4H), 2.93 (q, J=6.6 Hz, 2H), 2.19 (t, J=7 Hz, 2H), 1.59 (m, 4H), 1.49 (m, 4H), 1.40 (s, 9H), 1.38 (s, 9H), 1.36 (m, 2H).

Example 2

This example demonstrates preparation of isomerically pure bromo-substituted rhodamine dyes as shown in Schemes 2 and 3.
Synthesis of Bromo-Substituted Dyes (5) and (6).

A mixture of 8-hydroxyjulolidine (10 g, 52.8 mmol), 4-bromophthalic anhydride (4.8 g, 21.1 mmol), propionic acid (75 mL) and methanesulfonic acid (0.5 mL) was heated at reflux for 22 hrs. The resultant dark mass was dissolved in dichloromethane (~1 L), washed with water, saturated sodium chloride and dried over Na$_2$SO$_4$. The solution was concentrated to give a crude mixture of 5 and 6. The isomers were separated by three repetitive silica gel chromatographies eluting with a gradient of MeOH (0 to 15%) in dichloromethane. Concentration of the faster eluting product and slower eluting product afforded 2.56 g of compound 6 and 3.72 g of compound 5, correspondingly. (5) H$^1$-NMR (DMSO-d6): δ 7.90 (d, J=8.7 Hz, 1H), 7.83 (dd, J$_1$=8 Hz, J$_2$=1.5 Hz, 1H), 7.44 (d, J=1.5 Hz, 1H), 6.20 (s, 2H), 3.24 (m, 4H), 2.88 (t, J=6 Hz, 2H), 2.54 (t, J=6 Hz, 2H), 1.96 (m, 2H), 1.80 (m, 2H). (6) H$^1$-NMR (DMSO-d6): δ 8.11 (d, J=1.5 Hz, 1H), 7.77 (dd, J$_1$=8 Hz, J$_2$=1.5 Hz, 1H), 7.09 (d, J=8 Hz, 1H), 3.32 (m, 4H), 2.92 (t, J=6 Hz, 2H), 2.65 (t, J=6 Hz, 2H), 1.98 (m, 2H), 1.82 (m, 2H).
Synthesis of Benzophenones (7) and (8) (Isomeric Mixture).

8-Hydroxyjulolidine (10 g, 52.8 mmol), 4-bromophthalic anhydride (12.6 g, 55.5 mmol) and toluene were combined and heated at 120° C. (bath temperature) with stirring for 2 h. The mixture was cooled and run through a short silica gel column eluting with 0 to 5% MeOH in CH$_2$Cl$_2$ to remove pink-colored dye impurity. Evaporation of the solvent afforded 18.4 g of a mixture of 7 and 8 as a yellow, amorphous solid.
Synthesis of Compounds (2) and (10).

The mixture of compounds 7 and 8 from the previous step was dissolved in 200 mL of 1.25 M HCl in methanol. The solution was heated at 70° C. (bath temperature) for 12 h and concentrated. The residue was dissolved in ethyl acetate, washed with dilute sodium bicarbonate, saturated NaCl and dried over Na$_2$SO$_4$. Concentration afforded 18.0 g of isomeric mixture of 9 and 10. Fractional crystallization from methanol afforded pure isomers. (9): H$^1$-NMR (DMSO-d6): δ 12.73 (s, 1H), 7.85 (m, 2H), 7.63 (d, J=1.5 Hz, 1H), 6.39 (s, 1H), 3.68 (s, 3H), 3.26 (m, 4H), 2.59 (t, J=6.3 Hz, 2H), 2.43 (t, J=6.3 Hz, 2H), 1.85 (m, 2H), 1.76 (m, 2H). (10): H$^1$-NMR (DMSO-d6): δ 12.80 (s, 1H), 8.06 (d, J=2 Hz, 1H), 7.91 (dd, J$_1$=8 Hz, J$_2$=2 Hz, 1H), 7.36 (d, 8 Hz, 1H), 6.44 (s, 1H), 3.69 (s, 3H), 3.26 (m, 4H), 2.59 (t, J=6 Hz, 2H), 2.43 (t, J=6 Hz, 2H), 1.84 (m, 2H), 1.76 (m, 2H).
Conversion of Compound (9) into (7).

Compound 9 (1.8 g, 4.36 mmol) was dissolved in a mixture of THF (36 mL), 1N NaOH (36 mL) and methanol (18 mL). The solution was heated at 50° C. for 3 hrs and concentrated. The residue was partitioned between ethyl acetate and 10% citric acid. The organic layer was washed with saturated NaCl and dried over Na$_2$SO$_4$. Concentration of the solution afforded 1.7 g of the benzophenone intermediate 7 as a yellow amorphous solid.
Synthesis of Compound (11).

To a solution of 8-hydroxyjulolidine (3.8 g, 20 mmol) in 6 mL of DMF at 100° C. was added solid 3-imino-6-bromo-1H-isoindol-1-one hydrochloride (U.S. Pat. No. 4,900,739) (5.2 g, 200 mmol). Temperature was raised to 120° C. at which point the mixture turned dark and viscous. DMF (4 mL) was added and the reaction was heated at 120° C. for 3 h and then cooled. Black material was suspended in water and filtered. The resultant solid was re-suspended in methanol (75 mL). Filtration and drying under vacuum afforded 6.25 g (79%) of compound 11 as a black solid. H$^1$-NMR (DMSO-d6): δ 8.04 (d, J=8.4 Hz, 1H), 7.99 (d, J=1.8 Hz, 1H), 7.91 (dd, J$_1$=8.1 Hz, J$_2$=1.8 Hz, 1H), 7.49 (s, 1H), 3.37 (m, 4H), 2.74 (m, 2H), 2.45 (m, 2H), 1.87 (m, 2H), 1.81 (m, 2H).
Conversion of Compound (11) into (8).

A mixture of compound 11 (6.2 g, 15.6 mmol), 20% NaOH (25 mL) and iso-amyl alcohol (10 mL) was refluxed for 18 h. The reaction was cooled, concentrated to remove iso-amyl alcohol and acidified with conc. HCl to pH of 4. The resultant mixture was extracted with ethyl acetate (2×250 mL), the extract was washed with saturated NaCl dried over Na$_2$SO$_4$ and concentrated to afford 6.6 g of the desired benzophenone 8 as a yellow solid. H$^1$-NMR (DMSO-d6): δ 12.97 (br s, 1H), 7.99 (d, J=1.8 Hz, 1H), 7.64 (dd, J$_1$=8 Hz, J$_2$=1.8 Hz, 1H), 7.11 (d, J=8 Hz, 1H), 6.36 (s, 1H), 3.22 (m, 4H), 2.57 (t, J=6 Hz, 2H), 2.40 (t, J=6 Hz, 2H), 1.84 (m, 2H), 1.75 (m, 2H).
Synthesis of Compound (6) from (8).

A mixture of 8 (0.416 g, 1 mmol), 8-hydroxyjuloidine (0.21 g, 1.1 mmol) and methanesulfonic acid (1.5 mL) was heated at 170° C. for 2 hrs. The resulting dark purple viscous solution was cooled and combined with 50 mL of water to precipitate the product. The suspension was treated with 50% NaOH to pH of 3-4. The solid was collected by filtration washed with water, dried, washed with ether (to remove excess 8-hydroxyjulolidine) and dried again to afford 0.40 g of 6 as a dark purple solid.

Example 3

Preparation of Compound 12

A mixture of bromo-substituted dye 5 (0.85 g, 1.5 mmol), DMF (2.2 mL), N-ethylmorpholine (1 mL, 7.9 mmol) and phosphate 3 (1.27 g, 3 mmol) was degassed under vacuum for about 3 min. Tetrakis(triphenylphosphine)palladium(0) (0.12 g, 0.1 mmol) was added and the reaction was heated at 70° C. with stirring for 3 h. The reaction was cooled diluted with 10% MeOH in dichloromethane and loaded on a silica gel column with had been pre-equilibrated with the same solvent mixture. Elution with a gradient of MeOH (10→30%) in $CH_2Cl_2$ followed by concentration of the pure product fractions afforded 0.65 g of the desired phosphonate-substituted dye 12 as an amorphous solid.

Preparation of Compound 15.

Compound 12 (0.6 g, 0.66 mmol) was dissolved in 10 mL of anhydrous DMF and treated with 0.5 mL (3.6 mmol) of triethylamine followed by 0.2 mL (1.16 mmol) of pentafluorophenyl trifluoroacete (PFP-TFA). The reaction mixture immediately changed its color from blue-purple to blue indicating the formation of the PFP ester 13. After about 30 min diethylamine (0.5 mL, 4.8 mmol) was added and the reaction was allowed to proceed for another 30 min. Complete conversion of the PFP ester to the amide 14 was confirmed by reverse-phase HPLC. A mixture of $CH_2Cl_2$ (10 mL) and TFA (10 mL) was added, the reaction was kept at room temperature for 1 h and concentrated. A mixture of MeOH (10 mL) and triethylamine (10 mL) was added. After being stirred at 60° C. for 1 h, the reaction was concentrated and chromatographed on silica eluting with a gradient of MeOH (10→40%) in $CH_2Cl_2$ containing 10% triethylamine. Concentration of the pure product fractions afforded 0.25 g of the desired dye 15 as a dark-purple, amorphous solid.

Preparation of Compound 16.

Triethylamine (0.1 mL, 0.72 mmol) and PFP-TFA (0.1 mL, 0.58 mmol) were added to a solution of 15 (0.25 g, 0.3 mmol) in 5 mL of anhydrous $CH_2Cl_2$. After 1 h the reaction was diluted with $CH_2Cl_2$ (50 mL), washed with 10% citric acid and saturated NaCl. The organic layer was dried over $Na_2SO_4$ and concentrated. The resultant oil was triturated in ether/hexane mixture to remove pentafluorophenol and co-evaporated with $CH_2Cl_2$ to afford 0.25 g of the desired PFP ester 16 as an amorphous, black-purple solid.

Example 4

Preparation of Compound 21

To a solution of 6 (1.0 g, 1.76 mmol) in 50 mL of DMF at 0° C. was added thionyl chloride (0.64 mL, 8.8 mmol). After being stirred for 1 h at 0° C., the reaction was concentrated and re-dissolved in 50 mL of DMF. The solution was cooled to −20° C. and treated with a mixture of triethylamine (2.45 mL, 17.6 mmol) and N-methylaminoethanol (0.707 mL, 8.8 mmol). The reaction was stirred at −20° C. for 2 hrs and concentrated. The residue was dissolved in dichloromethane and extracted with 0.5 M HCl, saturated NaCl and then dried over $Na_2SO_4$. The crude material was chromatographed on silica eluting with dichloromethane containing methanol (from 0 to 15%) and 2% acetic acid. The pure product fractions were concentrated, re-dissolved in dichloromethane and washed with saturated NaCl. The organic layer separated, dried over $Na_2SO_4$ and concentrated to afford 0.95 g of the carboxamide-substituted dye 21.

Preparation of Compound 22.

Compound 21 (0.90 g, 1.3 mmol), DMF (20 mL), 4-ethyl morpholine (1.33 mL, 10.48 mmol) and phosphate 4 (0.818 g, 1.97 mmol) were combined and degassed under vacuum for 1-2 min. Tetrakis(triphenylphosphine)palladium (0) (0.453 g, 0.393 mmol) was added and the reaction was heated at 70° C. for 2.5 hrs. The solvent was evaporated under vacuum and the residue was re-dissolved in ~15 mL of dichloromethane. The mixture was loaded onto a silica gel column and eluted with a gradient of methanol (15 to 30%) in ethyl acetate (plus 2% 0.6 M KI in water). The pure product fractions were combined and concentrated. The residue was re-dissolved in dichloromethane and washed with saturated NaCl. The organic layer separated, dried over $Na_2SO_4$ and concentrated to afford 0.95 g of the phosphonate-substituted intermediate 22 as a dark purple, amorphous solid. $^{31}$P NMR (DMSO-d6): δ 24.85 and 24.62 (mixture of rotomers)

Preparation of Compound 23.

Compound 23 was prepared by adding 4-nitrophenyl chloroformate to compound 22 in the presence of triethylamine. The product was purified using flash chromatography on silica gel.

Example 5

Preparation of Compounds (24) and (25)

20 g (88.9 mmol) of 4-bromophthalic anhydride were introduced into a mixture of 19.6 g (178 mmol) of resorcinol and 44 g of phosphorus oxychloride within a period of 30 min at a temperature of 50-55° C. The resulting mixture was stirred at 55° C. for 16 h, and then heated within 1 h to a temperature of 110° C. This temperature was maintained for 2 hrs. The reaction mixture was then cooled to 80° C. and introduced into a mixture of 700 mL of water and 100 g of sodium hydroxide solution (33% by weight) having a temperature of about 70° C., whereby the rate of introduction was chosen such that the reaction mixture gently boiled while refluxing. The mixture was cooled and extracted with ethyl acetate (3×500 mL). The extract was washed with saturated sodium chloride solution and dried over anhydrous sodium sulfate. The solution was filtered and concentrated to afford 16.5 g of a mixture of compounds 24 and 25. The isomers were separated by silica gel chromatography eluting with 1:1 hexane:dichloromethane. Yields of pure isomers were 5.5 g and 7.4 g, correspondingly for 24 and 25. Compound 24: $H^1$-NMR (DMSO-d6): δ 8.23 (d, J=2 Hz, 1H), 7.98 (dd, $J_1$=8 Hz, $J_2$=2 Hz, 1H), 7.57 (d, J=2 Hz, 2H), 7.36 (d, J=8 Hz, 1H), 7.20 (dd, $J_1$=8.7 Hz, $J_2$=2 Hz, 2H), 6.97 (d, J=8.7 Hz, 2H). Compound 25: $H^1$-NMR (DMSO-d6): δ 7.96 (m, 2H), 7.77 (d, J=2 Hz, 1H), 7.56 (d, J=2 Hz, 2H), 7.36 (d, J=8 Hz, 1H), 7.20 (dd, $J_1$=8.7 Hz, $J_2$=2 Hz, 2H), 6.95 (d, J=8.7 Hz, 2H).

Preparation of Compounds (26).

A mixture of compound 25 (2.0 g, 4.5 mmol), $ZnCl_2$ (2.6 g, 22.8 mmol), tributylamine (2 mL), N-methylaminoethane sulfonic acid, sodium salt (5.3 g, 33 mmol) and 1-methyl-2-pyrrolidinone was heated with stirring at 160° C. for 9 hrs. The reaction was cooled, dissolved in warm methanol (~50 mL) and loaded onto a silica gel column (6×40 cm), which had been pre-equilibrated with 10% of each methanol and triethylaamine in dichloromethane. The column was eluted with dichloromethane followed by a gradient of methanol (from 0 to 20%) in dichloromethane containing 10% triethylamine. The pure product fractions were collected and concentrated to afford 2.1 g of 26 (triethylammonium salt) as a purple solid.

Preparation of Compound (27).

To a solution of compound 26 (1.7 g, 2 mmol) in a mixture of DMF (10 mL) and water (3 mL) were added N-ethylmorpholine (3.3 mL, 26 mmol) and phosphate 3 (2.1 g, 5 mmol). The mixture was degassed for about 1 min in vacuo. Tetrakis-triphenylphosphine palladium (0) (0.46 g, 0.4 mmol) was added, and the reaction was stirred with heating at 90° C. for 30 min. The reaction was concentrated and loaded onto a silica gel column, which had been pre-equilibrated with 10% MeOH, 10% triethylamine in dichloromethane. The column was washed with a dradient of MeOH (0 to 20%) in dichloromethane containing 10% triethylamine. Concentration of the product containing fractions afforded 0.9 g of phosphonate-substituted dye 27 as a purple, hygroscopic solid.

Preparation of Compound (29).

To a solution of compound 27 (0.8 g, 0.67 mmol) in 12 mL of anhydrous dichloromethane was added triethylamine (0.4 mL, 2.9 mmol) followed by PFP-TFA (2×0.2 mL, 2.33 mmol). The formation of the PFP ester 28 was confirmed by HPLC analysis. After being stirred at room temperature for 1 h, the reaction was treated with morpholine (0.5 mL, 5.7 mmol) and loaded onto a silica gel column, which had been pre-equilibrated with 5% MeOH, 10% triethylamine in dichloromethane. The column was washed with a gradient of MeOH (5 to 10%) in dichloromethane containing 10% of triethylaamine. Concentration of the product containing fractions afforded 0.45 g of carboxamide dye 29 as an amorphous solid.

Preparation of Compound (3).

To a solution of 29 (0.45 g) in 10 mL dichloromethane was added 10 mL of TFA. After being kept at room temperature for 1 h, the reaction was concentrated and re-dissolved in a mixture of methanol (10 mL) and water (10 mL). Triethylamine (2 mL) was added and the reaction was heated at 50° C. for 2 h. The solvents were evaporated and the resultant residue was chromatographed on DEAE Sephadex eluting with a gradient of LiCl. The pure product fractions were concentrated to an oil (mixture of 30 and LiCl). The oil was triturated in acetone, and the resulting precipitate was collected by centrifugation. The solid was washed with acetone and dried to afford 0.19 g of compound 30 (lithium salt). $^1$H NMR (D$_2$O) δ 7.92 (ddd, J$_1$=12 Hz, J$_2$=7.8 Hz, J$_3$=1.2 Hz, 1H), 7.77 (dd, J$_1$=12 Hz, J$_2$=1.2 Hz, 1H), 7.61 (dd, J$_1$=7.8 Hz, J$_2$=3 Hz, 1H), 7.12 (d, J=9.6 Hz, 2H), 6.89 (dd, J$_1$=9.6 Hz, J$_2$=2.4 Hz, 2H), 6.70 (d, J=2.4 Hz, 2H), 3.84 (m, 4H), 3.75 (m, 2H), 3.27 (m, 6H), 3.19 (m, 2H), 3.10 (s, 6H), 3.07 (t, J=7 Hz, 4H), 3.95 (t, J=7.5 Hz, 2H), 1.45 (m, 2H), 1.29 (m, 2H), 1.16 (m, 2H).

Preparation of Compound (31).

To a solution of 30 (50 mg) in 1 mL of DMSO was added triethylamine (0.05 mL) followed by PFP-TFA (0.05 mL). After being kept at room temperature for 30 min, the reaction was diluted with a 2% solution of NaClO$_4$ in acetone (10 mL). The resultant solid was collected by centrifugation, washed with acetone (2×10 mL) and dried in vacuo to afford 46 mg of the PFP ester 31 (sodium salt) as a purple solid.

Example 6

Preparation of Dye-Oligonucleotide Conjugates

To a solution of 100 nmoles of 5'-(6)-aminohexyl-octa-deoxythymidylate in 0.1 mL of DMSO was added 2 μl of triethylamine followed by 10 μl of 0.1 M solution of either 16 or 31 in DMSO. After 2-5 hrs, the reactions were diluted with water and chromatographed on a C18 reverse phase HPLC column eluting with a gradient of CH$_3$CN (0.1 M triethylammonium bicarbonate buffer, pH 8-9). The pure conjugate fractions were dried in a SpeedVac evaporator and reconstituted in water.

What is claimed is:
1. A fluorescent dye reagent having the formula:

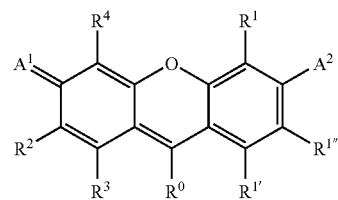

I wherein
A$^1$ is selected from the group consisting of O, N—Z' and N$^+$(Z')$_2$, wherein at each occurrence Z' is independently hydrogen, (C$_1$-C$_8$)alkyl, aryl-(C$_1$-C$_8$)alkyl, aryl or a protecting group; wherein the aliphatic or aryl portions of the Z' group are optionally substituted with halogen, sulfo, phosphono, alkylphosphono, (C$_1$-C$_4$)alkyl, aryl, L$^f$ or P$^Z$; or optionally the Z' group, at each occurrence, independently is combined with R$^2$ or R$^4$ to form a fused 5- to 7-membered ring, and the resultant fused 5- to 7-membered saturated or non-saturated ring is optionally fused to an aryl ring, and is optionally substituted with halogen, (C$_1$-C$_4$)alkyl, L$^f$ or P$^Z$;

A$^2$ is OR$^W$ or N(Z")$_2$, wherein each Z" is independently hydrogen, (C$_1$-C$_8$)alkyl, aryl(C$_1$-C$_8$)alkyl, aryl or a protecting group; wherein the aliphatic or aryl portions of the Z" group are optionally substituted with halogen, sulfo, phosphono, alkylphosphono, (C$_1$-C$_4$)alkyl, aryl, L$_f$ or P$_Z$; or optionally the Z" group, at each occurrence, independently is combined with R$^1$ or R$^{1''}$ to form a fused 5- to 7-membered ring wherein the resultant fused 5- to 7-membered saturated or non-saturated ring is optionally fused to an aryl ring, and is optionally substituted with halogen, C$_1$-C$_4$alkyl, aryl, L$^f$ or P$^Z$; and the substituent R$^W$ is selected from H, (C$_1$-C$_8$)alkyl, aryl, aryl (C$_1$-C$_4$)alkyl, a protecting group and L$^f$;

R$^{1'}$, R$^{1''}$, R$^2$, R$^3$ and R$^4$ are each independently selected from the group consisting of H, halogen, cyano, CF$_3$, sulfo, (C$_1$-C$_8$)alkyl, (C$_1$-C$_8$)alkylthio, (C$_1$-C$_8$)alkoxy, aryl, heteroaryl, L$^f$ and P$^Z$, wherein said aryl or heteroaryl group is optionally substituted with P$^Z$; or optionally any two of the R$^{1'}$, R$^{1''}$, R$^2$ and R$^3$ substituents that are attached to adjacent ring atoms are combined to form a five or six membered fused ring that is aromatic, non-aromatic or heteroaromatic, and is optionally substituted with P$^Z$; and the alkyl portions of any of R$^{1'}$, R$^{1''}$ and R$^1$ through R$^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; the aryl or heteroaryl portions of any of R$^{1'}$, R$^{1''}$ and R$^1$ through R$^4$ are optionally substituted with from one to four substituents selected from the group consisting of halogen, cyano, carboxy, sulfo, hydroxyl, amino, mono- or di(C$_1$-C$_6$)alkylamino, (C$_1$-C$_6$)alkyl, (C$_1$-C$_6$)alkylthio, (C$_1$-C$_6$)alkoxy, L$^f$ and P$^Z$;

R⁰ is selected from the group consisting of subformulae (a), (b), (c), and (d):

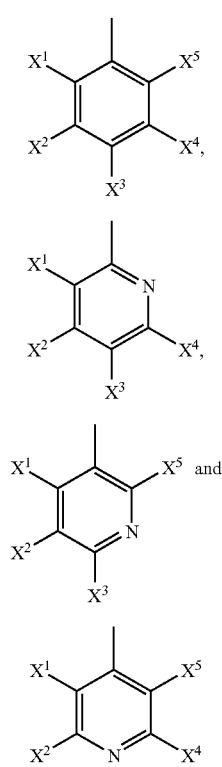

P^Z is a phosphonate group having a formula selected from (e), (f), (g) and (h):

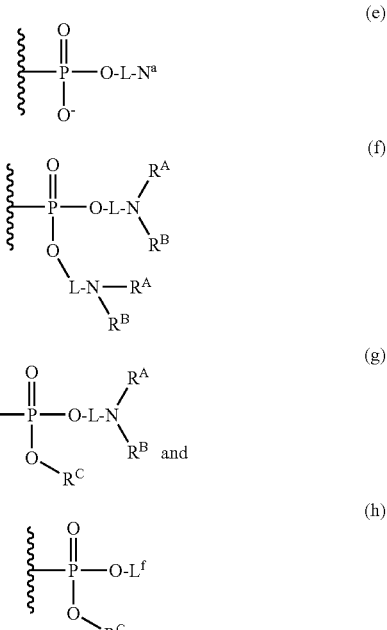

wherein $X^2$, $X^3$ and $X^4$ are each independently selected from the group consisting of H, amino, alkylamino, dialkylamino, isothiocyanate, amido, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, —$SO_3H$, —$PO_3H_2$, —$CO_2H$, $L^f$ and $P^Z$;

$X^1$ and $X^5$ are each independently selected from the group consisting of H, amino, alkylamino, dialkylamino, isothiocyante, amido, halogen, cyano, $CF_3$, $(C_1-C_8)$ alkyl, $(C_1-C_8)$alkoxy, $(C_1-C_8)$alkylthio, $(C_2-C_8)$alkenyl, $(C_2-C_8)$alkynyl, aryl, heteroaryl, $SO_2N(R^a)_2$ and CON $(R^a)_2$, and at least one of $X^1$ and $X^5$ is $SO_2N(R^a)_2$ or $CON(R^a)_2$, wherein each $R^a$ is independently selected from H, $(C_1-C_8)$alkyl, hydroxyl$(C_1-C_8)$alkyl, protected hydroxy$(C_1-C_8)$alkyl, sulfoalkyl, phosphonoalkyl and alkylphosphonoalkyl or the two $R^a$ substituents together with the nitrogen atom to which they are attached form a 5- or 6-membered heterocyclic ring having one additional heteroatom selected from O or N; and optionally, any two adjacent substituents of $X^1$ to $X^5$ are combined to form an aromatic or heteroaromatic ring; wherein the aryl or heteroaryl portions of $R^0$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^Z$; and wherein in formula I, there are from 0 to 1 $L^f$ groups and from 1 to 4 $P^Z$ groups, preferably 1 to 2 $P^Z$ groups;

$L^f$ is a linking group having an attached member selected from the group consisting of a protected or unprotected functional group, a reactive group, a polyfunctional linking moiety, a phosphoramidite moiety and a solid support;

wherein the wavy line indicates the direct attachment to a sp² carbon of said fluorescent dye; L is a linking group; $N^a$ is an ammonium ion group; each of $R^A$ and $R^B$ is independently selected from the group consisting of H and a labile protecting group; each $R^C$ is selected from the group consisting of H, $(C_1-C_8)$alkyl, aryl, aryl$(C_1-C_4)$alkyl, a labile protecting group or an alkylene linking group having a distal hydroxyl or protected hydroxy group; and salts thereof.

2. The fluorescent dye reagent of claim 1, wherein $A^1$ is =$N^+[(C_1-C_8)$alkyl$]_2$ substituted with a member selected from the group consisting of sulfo, phosphono or alkylphosphono.

3. The fluorescent dye reagent of claim 2, wherein $A^1$ is =$N^+(CH_3)(CH_2CH_2SO_3)$.

4. The fluorescent dye reagent of claim 1 wherein $A^2$ is —$[(C_1-C_8)$alkyl$]_2$ substituted with a member selected from the group consisting of sulfo, phosphono or alkylphosphono.

5. The fluorescent dye reagent of claim 3, wherein $A^2$ is —$N(CH_3)(CH_2CH_2SO_3)$.

6. The fluorescent dye reagent of claim 1, wherein R0 is subformula (a).

7. A The fluorescent dye reagent of claim 1, wherein $R^0$ is subformula (a), $X^5$ is —$CON(R^a)_2$ wherein each $R^a$ is independently selected from H, $(C_1-C_8)$alkyl, hydroxyl$(C_1-C_8)$alkyl and protected hydroxyl$(C_1-C_8)$alkyl; and one of $X^2$, $X^3$ and $X^4$ is $P^z$.

8. The fluorescent dye reagent of claim 1, wherein $R^0$ is subformula (a), $X^5$ is —$CON(R^a)_2$ wherein each $R^a$ is independently selected from H, $(C_1-C_8)$alkyl, hydroxyl$(C_1-C_8)$alkyl and protected hydroxyl$(C_1-C_8)$alkyl; and one of $X^2$, $X^3$ and $X^4$ is $P^z$; and $A^1$ is O and $A^2$ is $OR^w$.

9. The fluorescent dye reagent of claim 1 having formula I(a) or I(b):

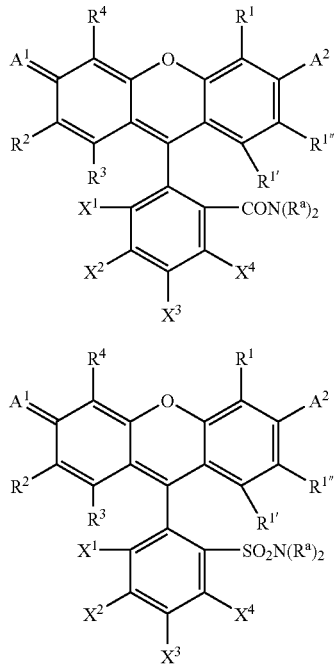

wherein
$R^{1'}$, $R^{1''}$, $^{R1}$, $R^2$, $R^3$ and $R^4$ are each independently selected from H, halogen, cyano, sulfo, aryl, heteroaryl, $CF_3$, $(C_1-C_8)$alkyl, $(C_1-C_8)$alkylthio, $(C_1-C_8)$alkoxy, $L^f$ and $P^Z$, wherein the alkyl portions of any of $R^{1'}$, $R^{1'''}$ $^{and\ R1}$ through $R^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms and the aryl or heteroaryl portions of any of $R^{1'}$, $R^{1''}$ and $R^1$ through $R^4$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^Z$; $X^1$ is selected from the group consisting of H, amino, alkylamino, dialkylamino, isothiocyanate, amido, halogen, cyano, $CF^3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_2N(R^a)_2$ and $CON(R^a)_2$, wherein each $R^a$ is independently selected from H, $(C_1-C_8)$alkyl, hyroxy$(C_1-C_8)$alkyl, protected hydroxyl$(C_1-C_8)$alkyl, aryl-OC(=O)O$(C_1-C_8)$alkyl, sulfoalkyl, phosphonoalkyl and alkylphosphonoalkyl, or the two $R^a$ substituents together with the nitrogen atom to which they are attached form a 5- or 6-membered heterocyclic ring having one additional heteteroatom selected from O or N;
$X^2$, $X^3$ and $X^4$ are each independently selected from the group consisting of H, amino, alkylamino, dialkylamino, isothiocyanate, amido, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, $L^f$ and $P^Z$ and optionally, any two adjacent $X^1$ through $X^4$ are combined to form an aromatic or heteroaromatic ring that is optionally further substituted with from one to four substituents selected from halogen cyano, carboxy, sulfo, hydroxyl, amino, mono- or di$(C_1-C_6)$alkylamino, $(C_1-C_6)$alkyl, $(C_1-C_6)$alkylthio, $(C_1-C_6)$alkoxy, $L^f$ and $P^Z$.

10. The fluorescent dye reagent of claim 9, wherein one of $X^2$, $X^3$, and $X^4$ is $P^Z$.

11. The fluorescent dye reagent of claim 1, having formula Ic:

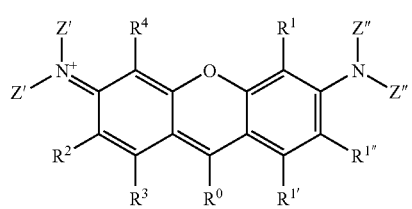

wherein the groups Z' and Z", at each occurrence, are independently selected from the group consisting of hydrogen, $(C_1-C_8)$alkyl, aryl-$C_1-C_8$ alkyl and aryl, wherein the aliphatic or aryl portions of the Z' or Z" groups are optionally substituted with halogen, sulfo, phosphono, alkylphosphono, $(C_1-C_4)$alkyl, aryl, $L^f$ and $P^Z$; and optionally the Z' group, at each occurrence is independently combined with $R^2$ or $R^4$ to form a fused 5- or 6-membered saturated or non-saturated ring, and optionally, the Z" group, at each occurrence is independently combined with $R^1$ or $R^{1*}$ to form a fused 5- or 6-membered saturated or non-saturated ring; wherein if present, said fused 5- or 6-membered ring is optionally fused to an aryl ring and is substituted with halogen, $(C_1-C_4)$alkyl, $L^f$ or $P^Z$.

12. The fluorescent dye reagent of claim 11, wherein $R^0$ is subformula (a) and $X^5$ is —$CON(R^a)_2$ wherein each $R^a$ is independently selected from H, $(C_1-C_8)$alkyl, hydroxyl$(C_1-C_8)$alkyl and protected hydroxyl$(C_1-C_8)$alkyl.

13. The fluorescent dye reagent of claim 11, wherein $R^0$ is subformula (a), $X^5$ is —$CON(R^a)_2$ wherein each $R^a$ is independently selected from H, $(C_1-C_8)$alkyl, hydroxyl$(C_1-C_8)$alkyl and protected hydroxyl$(C_1-C_8)$alkyl; and one of $X^2$, $X^3$ and $X^4$ is $P^Z$.

14. The fluorescent dye reagent of claim 11, wherein $R^0$ is subformula (a), $X^5$ is —$CON(R^a)_2$ wherein each $R^a$ is independently selected from H, $(C_1-C_8)$alkyl, hydroxyl$(C_1-C_8)$alkyl and protected hydroxyl$(C_1-C_8)$alkyl; one of $X^2$, $X^3$ and $X^4$ is $P^Z$; and each of $R^3$ and $R^1$ are hydrogen.

15. The fluorescent dye reagent of claim 11, selected from the group consisting of:

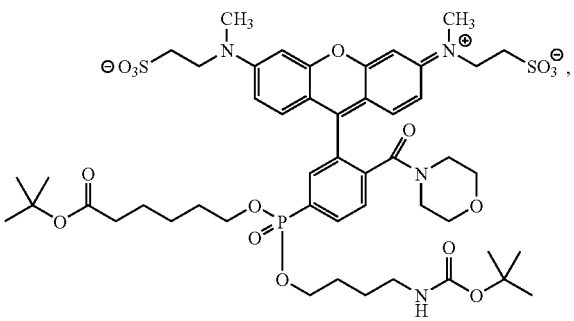

-continued

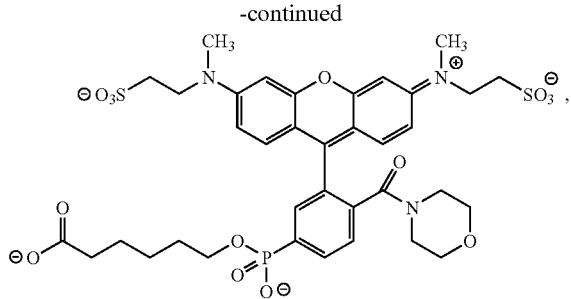

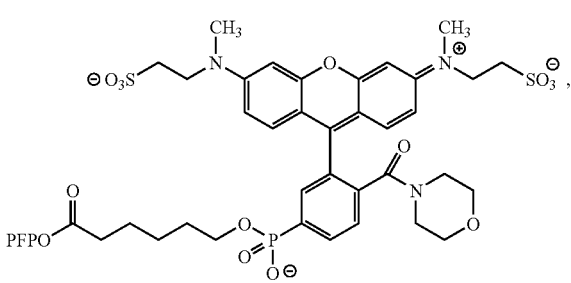

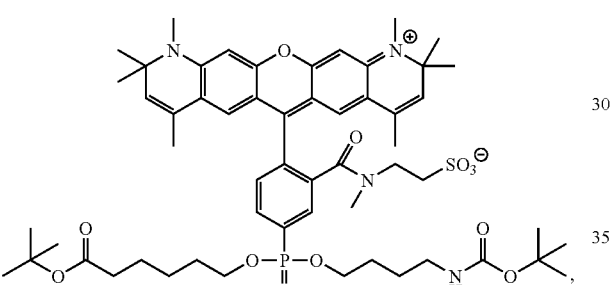

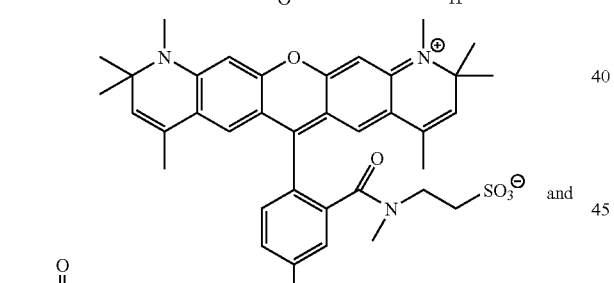

and

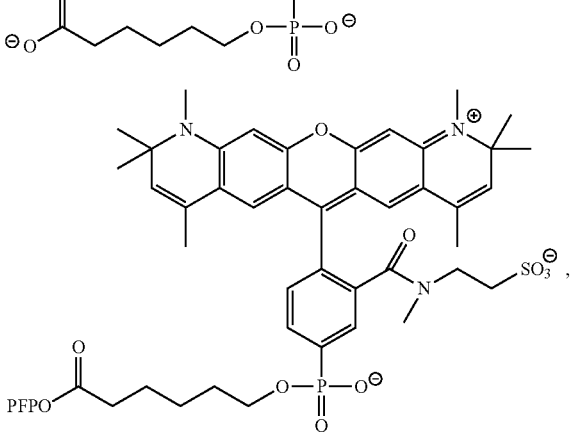

wherein PFP is pentafluorophenyl.

16. The fluorescent dye reagent of claim 11, selected from the group consisting of:

![Ic¹]

![Ic²]

![Ic³]

wherein in formulae $Ic^1$-$Ic^3$
each $X^5$ is $CON(R^a)_2$;
$R^{a'}$, $R^{b'}$, $R^{c'}$, $R^{d'}$, at each occurrence, is independently selected from the group consisting of hydrogen and ($C_1$-$C_6$)alkyl, or optionally, (i) any of $R^{b'}$, $R^{c'}$ and $R^{d'}$ represents a pair of methyl groups or (ii) any two substituents or $R^{b'}$, $R^{c'}$ and $R^{d'}$, that are attached to adjacent ring atoms are combined to form a fused 6-membered aryl ring, said fused ring is optionally substituted with $P^z$ or $L^f$; and each subscript k is independently an integer from 0-1.

17. The fluorescent dye reagent of claim 16, wherein one of $X^2$, $X^3$, and $X^4$ is $P^z$.

18. The fluorescent dye reagent of claim 16, having formula 1 c3, wherein each of $R^b$, $R^c$ and $R^d$ is hydrogen.

19. The fluorescent dye reagent of claim 16, having a structure selected from the group consisting of:

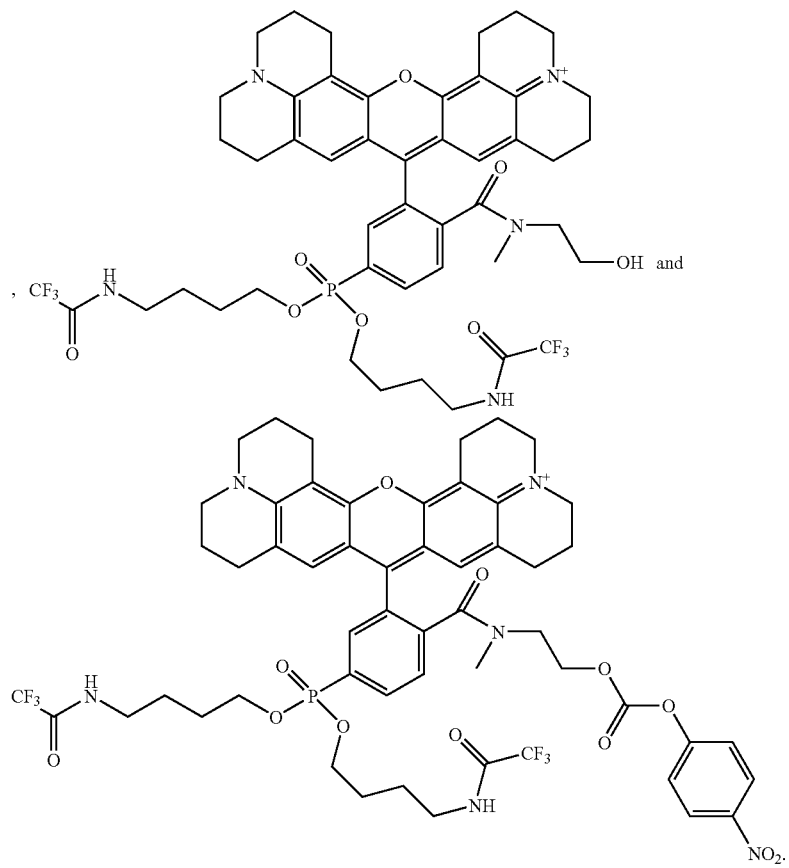
20. The fluorescent dye reagent of claim 16, having a structure selected from the group consisting of:
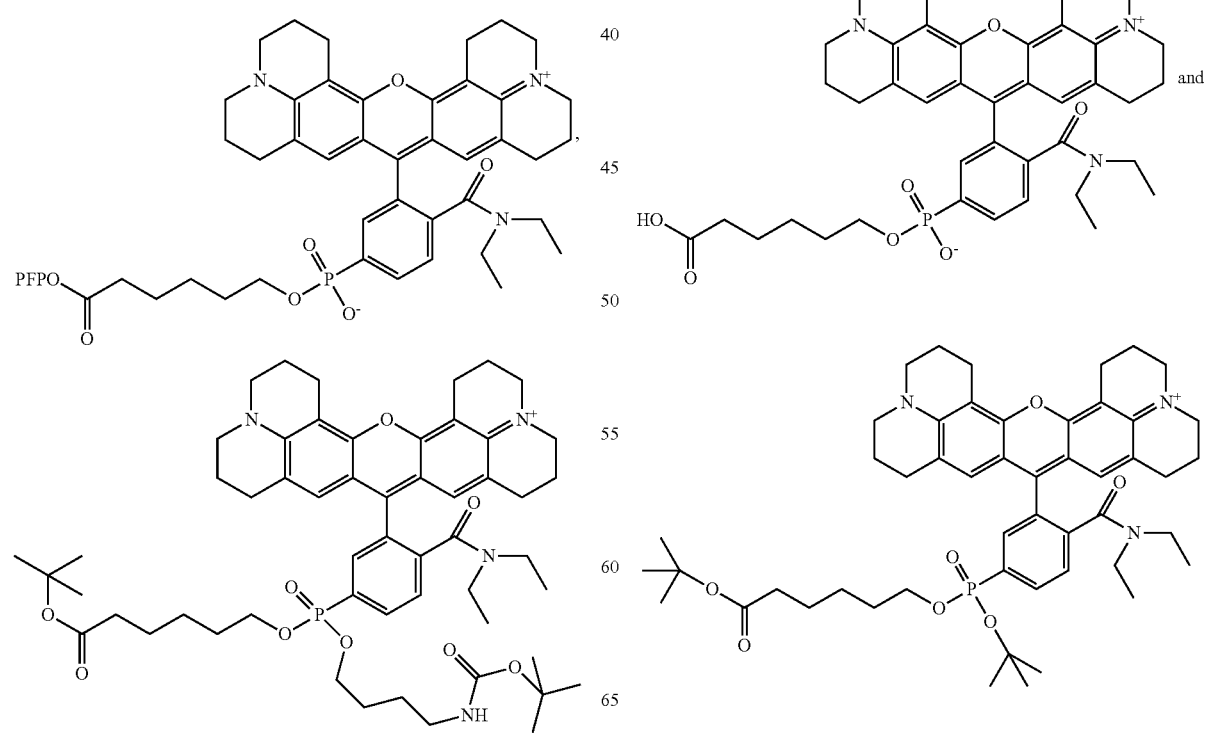
wherein PFP is pentafluorophenyl.

21. An oligonucleotide probe having an attached fluorescent dye reagent of claim 1, wherein attachment of the fluorescent dye reagent to the oligonucleotide is through a functional group present on Lf.

22. An oligonucleotide probe having an attached quencher and an attached fluorescent dye reagent of claim 1, wherein attachment of the fluorescent dye reagent to the oligonucleotide is through a functional group present on $L^f$.

23. An oligonucleotide probe having an attached quencher, minor groove binding agent, and an attached fluorescent dye reagent of claim 1, wherein attachment of the dye reagent to the oligonucleotide is through a functional group present on $L^f$.

24. An oligonucleotide probe having an attached fluorescent dye reagent of claim 1, wherein attachment of the fluorescent dye reagent to the oligonucleotide is through a functional group present on $P^z$.

25. An oligonucleotide probe having an attached quencher and an attached fluorescent dye reagent of claim 1, wherein attachment of the fluorescent dye reagent to the oligonucleotide is through a functional group present on $P^z$.

26. An oligonucleotide probe having an attached quencher, minor groove binding agent, and an attached fluorescent dye reagent of claim 1, wherein attachment of the fluorescent dye reagent to the oligonucleotide is through a functional group present on $P^z$.

27. A biological agent conjugate having an attached fluorescent dye reagent of claim 1, wherein attachment of the fluorescent dye reagent to the biological agent is through a functional group present on Lf.

28. A biological agent conjugate having an attached quencher and an attached fluorescent dye reagent of claim 1, wherein attachment of the fluorescent dye reagent to the biological agent is through a functional group present on $L^f$.

29. A biological agent conjugate having an attached quencher, minor groove binding agent, and an attached fluorescent dye reagent of claim 1, wherein attachment of the dye reagent to the biological agent is through a functional group present on $L^f$.

30. A biological agent conjugate having an attached fluorescent dye reagent of claim 1, wherein attachment of the fluorescent dye reagent to the biological agent is through a functional group present on $P^z$.

31. A biological agent conjugate having an attached quencher and an attached fluorescent dye reagent of claim 1, wherein attachment of the fluorescent dye reagent to the biological agent is through a functional group present on $P^z$.

32. A biological agent conjugate having an attached quencher, minor groove binding agent, and an attached fluorescent dye reagent of claim 1, wherein attachment of the fluorescent dye reagent to the biological agent is through a functional group present on $P^z$.

33. The conjugate of claim 27, wherein the biological agent is selected from the group consisting of a peptide, a protein, an enzyme substrate, a lipid, an oligosaccharide and a polysaccharide.

* * * * *